(12) United States Patent
Castillo et al.

(10) Patent No.: US 8,999,930 B2
(45) Date of Patent: Apr. 7, 2015

(54) SOLUBLE HYDROPHOBIC CORE CARRIER COMPOSITIONS FOR DELIVERY OF THERAPEUTIC AGENTS, METHODS OF MAKING AND USING THE SAME

(75) Inventors: Gerardo M. Castillo, Bothell, WA (US); Elijah M. Bolotin, Bothell, WA (US)

(73) Assignee: PharmaIN Corporation, Bothell, WA (US)

( * ) Notice: Subject to any disclaimer, the term of this patent is extended or adjusted under 35 U.S.C. 154(b) by 517 days.

(21) Appl. No.: 12/711,564

(22) Filed: Feb. 24, 2010

(65) Prior Publication Data
US 2010/0234279 A1    Sep. 16, 2010

Related U.S. Application Data

(63) Continuation of application No. 11/971,482, filed on Jan. 9, 2008, now abandoned.

(51) Int. Cl.
| | |
|---|---|
| *A61K 38/00* | (2006.01) |
| *A61K 38/22* | (2006.01) |
| *A61K 38/26* | (2006.01) |
| *A61K 47/48* | (2006.01) |
| *A61K 47/42* | (2006.01) |

(52) U.S. Cl.
CPC ..... *A61K 47/48315* (2013.01); *A61K 47/48038* (2013.01); *A61K 47/42* (2013.01)

(58) Field of Classification Search
CPC ................. A61K 47/48315; A61K 47/48038; A61K 47/42
USPC ........................... 514/9.7, 11.7; 530/308, 345
See application file for complete search history.

(56) References Cited

U.S. PATENT DOCUMENTS

| | | | |
|---|---|---|---|
| 4,857,311 | A | 8/1989 | Domb et al. |
| 5,118,666 | A | 6/1992 | Habener |

(Continued)

FOREIGN PATENT DOCUMENTS

| | | |
|---|---|---|
| EP | 0381446 B1 | 8/1994 |
| JP | 2002-194080 | 7/2002 |

(Continued)

OTHER PUBLICATIONS

Castillo et al., (Pharm Res. Jan. 2012;29(1):306-18. doi: 10.1007/s11095-011-0542-2. Epub Aug. 4, 2011).*

(Continued)

*Primary Examiner* — Cherie M Stanfield
(74) *Attorney, Agent, or Firm* — Christensen O'Connor Johnson Kindness PLLC

(57) ABSTRACT

The present invention relates to a soluble hydrophobic-core carrier composition comprising (i) a linear polymeric backbone; (ii) a plurality of hydrophilic polymeric protective chains covalently linked and pendant to the polymeric backbone and (iii) at least one hydrophobic moiety covalently linked and pendant to the polymeric backbone. In certain embodiments, the weight ratio of hydrophilic protective chains to hydrophobic moieties in the carrier is at least 15:1. In other embodiments, at least 90% of the residues of the polymeric backbone are coupled to a hydrophilic polymeric protective chain or a hydrophobic moiety. In other embodiments, the composition further comprises (iv) a hydrophobic load molecule dissociably linked to the hydrophobic moiety of the carrier.

27 Claims, 20 Drawing Sheets

(56) References Cited

U.S. PATENT DOCUMENTS

| | | |
|---|---|---|
| 5,120,712 A | 6/1992 | Habener |
| 5,527,524 A | 6/1996 | Tomalia et al. |
| 5,554,388 A | 9/1996 | Illum |
| 5,593,658 A | 1/1997 | Bogdanov et al. |
| 5,605,672 A | 2/1997 | Bogdanov et al. |
| 5,614,492 A | 3/1997 | Habener |
| 5,631,018 A | 5/1997 | Zalipsky et al. |
| 5,661,025 A | 8/1997 | Szoka, Jr. et al. |
| 5,663,387 A | 9/1997 | Singh |
| 5,681,544 A | 10/1997 | Schmitt-Willich et al. |
| 5,681,811 A | 10/1997 | Ekwuribe |
| 5,714,166 A | 2/1998 | Tomalia et al. |
| 5,744,166 A | 4/1998 | Illum |
| 5,763,585 A | 6/1998 | Nag |
| 5,837,747 A | 11/1998 | Soon-Shiong et al. |
| 5,871,710 A | 2/1999 | Bogdanov et al. |
| 5,891,418 A | 4/1999 | Sharma |
| 5,958,909 A | 9/1999 | Habener |
| 5,977,084 A | 11/1999 | Szoka, Jr. et al. |
| 6,006,753 A | 12/1999 | Efendic |
| 6,051,549 A | 4/2000 | Roberts et al. |
| 6,113,946 A | 9/2000 | Szoka, Jr. et al. |
| 6,124,273 A | 9/2000 | Drohan et al. |
| 6,162,462 A | 12/2000 | Bolotin et al. |
| 6,274,175 B1 | 8/2001 | Gombotz et al. |
| 6,284,727 B1 | 9/2001 | Kim et al. |
| 6,338,859 B1 | 1/2002 | Leroux et al. |
| 6,348,069 B1 | 2/2002 | Vacanti et al. |
| 6,365,173 B1 | 4/2002 | Domb et al. |
| 6,395,299 B1 | 5/2002 | Babich et al. |
| 6,443,898 B1 | 9/2002 | Unger et al. |
| 6,447,753 B2 | 9/2002 | Edwards et al. |
| 6,458,373 B1 | 10/2002 | Lambert et al. |
| 6,468,532 B1 | 10/2002 | Hsei et al. |
| 6,492,560 B2 | 12/2002 | Wilbur et al. |
| 6,509,323 B1 | 1/2003 | Davis et al. |
| 6,521,736 B2 | 2/2003 | Watterson et al. |
| 6,576,254 B1* | 6/2003 | Uchegbu ............... 424/450 |
| 6,579,851 B2 | 6/2003 | Goeke et al. |
| 6,583,111 B1 | 6/2003 | DiMarchi et al. |
| 6,586,524 B2 | 7/2003 | Sagara et al. |
| 6,589,549 B2 | 7/2003 | Shih et al. |
| 6,627,228 B1 | 9/2003 | Milstein et al. |
| 6,703,037 B1 | 3/2004 | Hubbell et al. |
| 6,703,359 B1 | 3/2004 | Young et al. |
| 6,706,689 B2 | 3/2004 | Coolidge et al. |
| 6,747,006 B2 | 6/2004 | Efendic |
| 6,828,303 B2 | 12/2004 | Kim et al. |
| 6,849,708 B1 | 2/2005 | Habener |
| 6,894,024 B2 | 5/2005 | Coolidge et al. |
| 6,899,883 B2 | 5/2005 | Dupre |
| 6,982,248 B2 | 1/2006 | Coolidge et al. |
| 6,992,060 B2 | 1/2006 | Brand |
| 6,998,137 B2 | 2/2006 | Shih et al. |
| 7,101,843 B2 | 9/2006 | Glaesner et al. |
| 7,138,105 B2* | 11/2006 | Bolotin ............... 424/9.36 |
| 7,138,486 B2 | 11/2006 | Habener |
| 7,144,863 B2 | 12/2006 | DeFelippis et al. |
| 7,199,217 B2 | 4/2007 | DiMarchi et al. |
| 7,259,233 B2 | 8/2007 | Dodd et al. |
| 7,534,449 B2 | 5/2009 | Saltzman et al. |
| 7,589,169 B2* | 9/2009 | Bolotin ............... 530/308 |
| 7,635,463 B2* | 12/2009 | Bolotin et al. ......... 424/1.65 |
| 7,790,140 B2* | 9/2010 | Bolotin ............... 424/1.65 |
| 7,960,336 B2* | 6/2011 | Castillo et al. ......... 514/1.4 |
| 8,231,859 B2* | 7/2012 | Bolotin et al. ......... 424/1.65 |
| 8,257,682 B2* | 9/2012 | Bolotin et al. ......... 424/1.65 |
| 2003/0050237 A1 | 3/2003 | Kim et al. |
| 2003/0119734 A1 | 6/2003 | Flink et al. |
| 2003/0220251 A1 | 11/2003 | Knudsen et al. |
| 2003/0224974 A1* | 12/2003 | Bolotin ............... 514/6 |
| 2003/0229034 A1 | 12/2003 | Waugh et al. |
| 2004/0092432 A1 | 5/2004 | During et al. |
| 2004/0162241 A1 | 8/2004 | Efendic |
| 2004/0197369 A1 | 10/2004 | Hubbell et al. |
| 2004/0209803 A1 | 10/2004 | Baron et al. |
| 2004/0220105 A1 | 11/2004 | Jensen et al. |
| 2004/0235726 A1 | 11/2004 | Jakubowski et al. |
| 2004/0266683 A1 | 12/2004 | Hathaway et al. |
| 2005/0008661 A1 | 1/2005 | Fereira et al. |
| 2005/0014681 A1 | 1/2005 | Minamitake et al. |
| 2005/0143303 A1 | 6/2005 | Quay et al. |
| 2005/0148497 A1 | 7/2005 | Khan et al. |
| 2005/0159356 A1 | 7/2005 | Dong et al. |
| 2005/0215475 A1 | 9/2005 | Ong et al. |
| 2005/0239705 A1 | 10/2005 | Dake et al. |
| 2005/0260259 A1 | 11/2005 | Bolotin |
| 2006/0003935 A1 | 1/2006 | Pan et al. |
| 2006/0019874 A1 | 1/2006 | Radhakrishnan et al. |
| 2006/0030838 A1 | 2/2006 | Gonnelli |
| 2006/0057137 A1 | 3/2006 | Steiness |
| 2006/0093660 A1* | 5/2006 | Bolotin ............... 424/450 |
| 2006/0128627 A1 | 6/2006 | Goke et al. |
| 2006/0172001 A1 | 8/2006 | Ong et al. |
| 2006/0178304 A1 | 8/2006 | Juul-Mortensen et al. |
| 2006/0183682 A1 | 8/2006 | Juul-Mortensen |
| 2006/0199763 A1 | 9/2006 | Knudsen et al. |
| 2006/0233857 A1 | 10/2006 | Amsden et al. |
| 2006/0247167 A1 | 11/2006 | Schlein et al. |
| 2006/0286129 A1 | 12/2006 | Sarubbi |
| 2007/0041951 A1 | 2/2007 | Egan et al. |
| 2007/0141006 A1 | 6/2007 | Livoreil et al. |
| 2007/0141145 A1* | 6/2007 | Castillo et al. ......... 424/464 |
| 2007/0244296 A1 | 10/2007 | Tomalia et al. |
| 2007/0298006 A1 | 12/2007 | Tomalia et al. |
| 2009/0053169 A1 | 2/2009 | Castillo et al. |
| 2009/0176892 A1 | 7/2009 | Castillo et al. |

FOREIGN PATENT DOCUMENTS

| | | |
|---|---|---|
| WO | WO 97/33552 A1 | 9/1997 |
| WO | WO 98/42383 A1 | 10/1998 |
| WO | WO 03/072143 A2 | 9/2003 |
| WO | WO 03072143 A1 * | 9/2003 |
| WO | WO 2004/014451 A1 | 2/2004 |
| WO | WO 2004/022004 A2 | 3/2004 |
| WO | WO 2004/026912 A1 | 4/2004 |
| WO | WO 2004/022004 A3 | 12/2004 |
| WO | WO 2005/065714 A1 | 7/2005 |
| WO | WO 2005/084180 A2 | 9/2005 |
| WO | WO 2005/084180 A3 | 12/2005 |
| WO | WO 2005/115492 A1 | 12/2005 |
| WO | WO 2007/024899 A2 | 3/2007 |
| WO | WO 2007/030706 A1 | 3/2007 |
| WO | WO 2007/038964 A1 | 4/2007 |
| WO | WO 2007/048190 A1 | 5/2007 |
| WO | WO 2007/056681 A2 | 5/2007 |
| WO | WO 2007/076371 A2 | 7/2007 |
| WO | WO 2007/082331 A1 | 7/2007 |
| WO | WO 2007/024899 A3 | 11/2007 |
| WO | WO 2007/056681 A3 | 4/2008 |

OTHER PUBLICATIONS

Ahrén, et al. Improved glucose tolerance and insulin secretion by inhibition of dipeptidyl peptidase IV in mice. Eur. J. Pharmacol. 2000; 404(1-2):239-245.

Berklow, et al. Eds. The Merck Manual of Diagnosis and Therapy. Merck Laboratories. Merck & Co. Inc. Rahway, NJ. 1992.

Brand, et al. Pharmacological treatment of chronic diabetes by stimulating pancreatic beta-cell regeneration with systemic co-administration of EGF and gastrin. Pharmacol Toxicol. 2002; 91(6):414-420.

Bulotta, et al. Cultured pancreatic ductal cells undergo cell cycle re-distribution and beta-cell-like differentiation in response to glucagon-like peptide-1. J. Mol. Endocrinol. 2002; 29(3):347-360.

Buteau, et al. Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells. Diabetologia. 1999; 42(7):856-864.

Cadranel, et al. [Long-term efficacy and tolerability of omeprazole in 20 patients with severe Zollinger-Ellison syndrome] Gastroenterol Clin Biol. 1989; 13(8-9):654-662. (French with English Summary).

(56) References Cited

OTHER PUBLICATIONS

Caliceti, et al. Pharmacokinetic and biodistribution properties of poly(ethylene glycol)-protein conjugates. Advanced Drug Delivery Reviews. 2003; 55:1261-1277.

Chen, et al. A novel gene delivery system using EGF receptor-mediated endocytosis. FEBS Lett. 1994; 338(2):167-9.

Chowdhury, et al. Fate of DNA targeted to the liver by asialoglycoprotein receptor-mediated endocytosis in vivo. Prolonged persistence in cytoplasmic vesicles after partial hepatectomy. J Biol Chem. 1993; 268(15):11265-71.

Cras-Meneur, et al. Epidermal growth factor increases undifferentiated pancreatic embryonic cells in vitro: a balance between proliferation and differentiation. Diabetes 2001; 50(7):1571-1579.

Crutzfeldt, et al.Is Hypergastrinaemia dangerous to man? Scand J Gastroenterol Suppl. 1991;180:179-191.

Dash, et al. Synthetic polymers for vectorial delivery of DNA: characterisation of polymer-DNA complexes by photon correlation spectroscopy and stability to nuclease degradation and disruption by polyanions in vitro. Journal of Controlled Release. 1997; 48: 269-276.

Druncker. Enhancing incretin action for the treatment of type 2 diabetes. Diabetes Care. 2003; 26(10):2929-2940.

Erbacher, et al. The reduction of the positive charges of polylysine by partial gluconoylation increases the transfection efficiency of polylysine/DNA complexes. Biochim Biophys Acta. 1997; 1324(1):27-36.

Ettaro, et al. Cost-of-illness studies in diabetes mellitus. Pharmacoeconomics. 2004; 22(3):149-64.

Feng, et al. Tissue distribution and plasma clearance of heparin-binding EGF-like growth factor (HB-EGF) in adult and newborn rats. Peptides. 2006; 27:1589-1596.

Gilles, et al. Stability of water-soluble carbodiimides in aqueous solution. Anal Biochem. 1990; 184(2):244-8.

Hakanson, et al. Evidence that gastrin enhances 45Ca uptake into bone through release of a gastric hormone. Regul Pept. 1990; 28(1):107-118.

Halter, et al. Effect of acid inhibition on the growth of parietal cells. Scand J Gastroenterol Suppl. 1986; 125:9-13.

Hansen, et al. Pharmcokinetics and organ metabolism of carboxyamidated and glycine-extended gastrins in pigs. Am J Physiol. 1996; 271:G156-163.

Hrkach, et al. Poly(L-lactic acid-co-amino acid) Graft Copolymers: A Class of Functional Biodegradable Biomaterials. Hydrogel and Biodegradable Polymers for Bioapplications. Acs Symposium Series No. 627. Ottenbrite, et al. Eds. American Chemical Society. Chapter 8. 1996; 93-101.

Hrkach, et al. Synthesis of poly(L-lactic acid-co-L-lysine) graft copolymers. Macromolecules. 1995; 28: 4736-9.

Hudecz, et al. Influence of carrier on biodistribution and in vitro cytotoxicity of methotrexate-branched polypeptide conjugates. Bioconjug Chem. 1993; 4(1):25-33.

Huotari, et al. Growth factor-mediated proliferation and differentiation of insulin-producing INS-1 and RINm5F cells: identification of betacellulin as a novel beta-cell mitogen. Endocrinology. 1998; 139(4):1494-1499.

Im, et al. Irreversible inactiviation of rat gastric (H+-K+)-ATPase in vivo by omeprazole. Biochem Biophys Res Commun. 1985; 126(1):78-82.

International Search Report for PCT/US03/05937 completed on Jun. 16, 2003 and mailed on Jul. 24, 2003 (4 pages).

Keeling, et al. Studies on the mechanism of action of omeprazole. Biochem Pharmacol. 1985; 34(16):2967-2973.

Klinkenberg-Knol, E. The role of omeprazole in healing and prevention of reflux disease. Hepatogastroenterology. 1992; 39:27-30.

Kollen, et al. Gluconoylated and glycosylated polylysines as vectors for gene transfer into cystic fibrosis airway epithelial cells. Hum Gene Ther. 1996; 7(13):1577-86.

Koop, et al. Serum gastrin levels during long-term omeprazole treatment. Aliment Pharmacol Ther. 1990; 4(2):131-138.

Krakowski, et al. Transgenic expression of epidermal growth factor and keratinocyte growth factor in beta-cells results in substantial morphological changes. J Endocrinol. 1999; 162:167-175.

Lamberts, et al. Long-term omeprazole treatment in man: effects on gastric endocrine cell populations. Digestion. 1988; 39(2):126-135.

Lapidot, et al. Use of esters of N-hydroxysuccinimide in the synthesis of N-acylamino acids. J Lipid Res. 1967; 8(2):142-145.

Larson, et al. Omeprazole-induced hypergastrinemia: role of gastric acidity. J Surg Res. 1986; 40(5):504-509.

Larson, et al. Relationship of omeprazole-induced hypergastrinemia to gastric pH. Surgery. 1986; 100(2):175-180.

Lev-Ran, et al. Origin of urinary epidermal growth factor in humans: excretion of endogenous EGF and infused [131I]-human EGF and kidney histochemistry. Clin Exp Pharmacol Physiol. 1992; 19(10):667-673.

Nielsen, et al. Pharmacology of exenatide (synthetic exendin-4) for the treatment of type 2 diabetes. Curr. Opinion Investig. Drugs. 2003; 4(4):401-405.

Otto, et al. Recognition and separation of isoenzymes by metal chelates: Immobilized metal ion affinity partitioning of lactate dehydrogenase isoenzymes. Journal of Chromatography. 1993; 644: 25-33.

Perry, et al. The glucagon-like peptides: a double-edged therapeutic sword? Trends in Pharmacol. Sci. 2003; 24(7):377-383.

Schentag, et al. Pharmacokinetics and pharmacodynamics of acid-suppressive agents in patients with gastroesophageal reflux disease. Am J Hosp Pharm. 1993; 50: S7-10.

Scrocchi, et al. Identification of glucagon-like peptide 1 (GLP-1) actions essential for glucose homeostasis in mice with disruption of GLP-1 receptor signaling. Diabetes. 1998; 47(4):632-639.

Senekowitsch-Schmidtke, et al. In vivo evaluation of epidermal growth factor (EGF) receptor density on human tumor xenografts using radiolabeled EGF and anti-(EGF receptor) mAb 425. Cancer Immunol Immunother. 1996; 42(2): 108-114.

Shapiro, et al. Clinical islet transplant: current and future directions towards tolerance. Immunol. Rev. 2003; 196:219-36.

Song, et al. Expansion of Pdxl-expressing pancreatic epithelium and islet neogenesis in transgenic mice overexpression transforming growth factor alpha. Gastroenterology. 1999; 117(6):1416-1426.

Sparado, et al. A convenient manual trinitrobenzenesulfonic acid method for monitoring amino acids and peptides in chromatographic column effluents. Anal Biochem. 1979; 96:317-321.

Suarez-Pinzon, et al. Combination therapy with epidermal growth factors and gastrin increses beta-cells mass and reverses hyperglycemia in diabetic NOD mice. Diabetes. 2005; 54(9):2596-2601.

Suginoshita, et al. Liver targeting of interferon-β with a liver-affinity polysaccharide based on metal coordination in mice. Journal of Pharmacology and Experimental Therapeutics. 2001; 298(2): 805-11.

Terpe, K. Overview of tag protein fusions: from molecular and biochemical fundamentals to commercial systems. Appl Microbiol Biotechnol. 2003; 60: 523-33.

Urusova, et al. GLP-1 inhibition of pancreatic islet cell apoptosis. Trends Endocrinol Metab. 2004; 15(1):27-33.

Van Nieuwenhove, et al. Gastrin stimulates epithelial cell proliferation in the oesophagus of rats. Virchows Arch. 1998; 432(4): 371-375.

Wagner. Delivery of drugs, protein and genes into cells using transferrin as a ligand for receptor-mediated endocytosis. Advanced drug delivery reviews. 1994; 14: 113-135.

Wang, et al. Pancreatic gastrin stimulates islet differentiation of transforming growth factor alpha-induced ductular precursor cells. J Clin Invest. 1993; 92(3):1349-1356.

Wiedeman, et al. Dipeptidyl peptidase IV inhibitors for the treatment of impaired glucose tolerance and type 2 diabetes. Curr. Opinion Investig. Drugs. 2003; 4(4):412-420.

Xu, et al. Exendin-4 stimulates both beta-cell replication and neogenesis, resulting in increased beta-cell mass and improved glucose tolerance in diabetic rats. Diabetes. 1999; 48(12):2270-2276.

Yamamoto, et al. Recombinant human betacellulin promotes the neogenesis of beta-cells and ameliorates glucose intolerance in mice with diabetes induced by selective alloxan perfusion. Diabetes. 2000; 49(12):2021-2027.

(56) References Cited

OTHER PUBLICATIONS

Yu, et al. Pharmacokinetic and pharmacodynamic evaluation of a novel proton pump inhibitor, YH1885, in healthy volunteer. J Clin Pharmacol. 2004; 44(1):73-82.

Zhou, et al. DNA transfection mediated by cationic liposomes containing lipopolylysine: characterization and mechanism of action. Biochim Biophys Acta. 1994; 1189(2):195-203.

Zhou, et al. Lipophilic polylysines mediate efficient DNA transfection in mammalian cells. Biochim Biophys Acta. 1991; 1065(1):8-14.

International search report dated Nov. 23, 2007 for PCT Application No. PCT/US2006/62328.

International search report dated Feb. 24, 2009 for PCT Application No. US2009/30678.

International search report dated Feb. 26, 2009 for PCT Application No. US2009/30471.

Office action dated Dec. 15, 2009 for U.S. Appl. No. 11/613,183.

Office action dated Dec. 15, 2009 for U.S. Appl. No. 12/194,144.

Office action dated Jul. 20, 2009 for U.S. Appl. No. 11/428,803.

PharmaIn—Enabling and improving human therapeutics. PharmaIn Introduction. Oct. 2009. Available at www.pharmain.com/PDF/PharmaIN%20BD%20Presentation%20Slides_16OCT09.pdf. Accessed Mar. 24, 2010.

Porath, et al. Metal chelate affinity chromatography, a new approach to protein fractionation. Nature. Dec. 18, 1975;258(5536):598-9.

Castillo, et al. Long-acting GLP-1: formulation and in vitro evaluation. Diabetes. Jun. 2007; Supplement 1, vol. 56, pA127.

Castillo, et al. PGC-GLP-1: Pharmacokinetics in rodents. Diabetes. Jun. 2007; Supplement 1, vol. 56, pA554.

European search report and opinion dated Apr. 24, 2013 for EP Application No. 09700547.4.

Medarova, et al. Noninvasive magnetic resonance imaging of microvascular changes in type 1 diabetes. Diabetes. Aug. 2007; 56(11):2677-2682.

Reichstetter, et al Long acting GLP-1 for the treatment of type 1 diabetes. Diabetes. Jun. 2007; Supplement 1, vol. 56, pA73.

Reichstetter, et al Long acting GLP-1 for the treatment of type 2 diabetes. Diabetes. Jun. 2007; Supplement 1, vol. 56, pA144.

Office action dated Jun. 22, 2010 for U.S. Appl. No. 11/613,183.

Office action dated Nov. 8, 2012 for U.S. Appl. No. 11/613,183.

U.S. Appl. No. 14/087,523, filed Nov. 22, 2013, Castillo et al.

Office action dated May 23, 2013 for U.S. Appl. No. 11/613,183.

European search report and opinion dated Apr. 26, 2013 for EP Application No. 6846696.0.

\* cited by examiner isothiocyanate ... thiourea

Succinimidyl ester ... carboxamide isothiocyanate ... sulfonamide

1.

2.

3.

5:1 DCM / MeOH

Bromocresol / ninhydrin

SOLUBLE HYDROPHOBIC CORE CARRIER COMPOSITIONS FOR DELIVERY OF THERAPEUTIC AGENTS, METHODS OF MAKING AND USING THE SAME

CROSS-REFERENCE

This application is a continuation of U.S. patent application Ser. No. 11/971,482, filed on Jan. 9, 2008 now abandoned, which is herein incorporated by reference in its entirety and to which priority is claimed.

GOVERNMENTAL LICENSE RIGHTS

Work described herein was made in part with government support under 5 R43 DK069727 awarded by the National Institute of Diabetes and Digestive and Kidney Diseases (NIDDK). The U.S. Government may have certain rights in subject matter provided herein.

BACKGROUND OF THE INVENTION

The development of new drugs, formulations and other systems for administration of physiologically active peptides and proteins, and other hydrophobic drugs or therapeutics is driven by the need to achieve the desirable physiological effects. Peptides and proteins have been observed to be unstable in blood and the gastro-intestinal tract and therefore may need to be stabilized or protected prior to delivery and remain protected once in either the gastro-intestinal tract or the circulation. Once the active pharmaceutical gets into the systemic circulation, those that have low molecular masses tend to have short biological half-lives due to their efficient removal from systemic circulation via kidneys. Furthermore, a fraction of them can also be removed via reticuloendothelial uptake due to recognition by monocyte/macrophages or as a result of opsonization by complement components. They can also lose their activity in vivo due to proteases and other enzymes.

Existing drug delivery systems can, in part, circumvent these undesirable effects and can be useful for peptide and protein delivery in vivo, with certain shortcomings, as noted. First, a continuous systemic infusion of drug via a pump can be employed. This strategy is proven efficient in clinical practice but may be impractical for outpatients requiring high levels of mobility, associated disadvantages of quality of life and potential intravenous (I.V.) line infections.

Second, peptides and proteins can be included in an implantable pump comprised of a capsule with a membrane allowing diffusion of the drug, for example, at a desirable release rate. Due to limited volume of these capsules, peptides and proteins are often used in a concentrated formulation which leads to a loss of solubility due to aggregation and potential loss of specific activity. In most cases, the drug is usually released into the extracellular space and distributed in lymphatics. Overall concentration of peptide or protein may be affected by local lymph node activity and the efficacy of lymph node drainage of the implantation site. There is also a potential of host reaction to capsule material but in general, this side effect is infrequent.

Third, the drug release system can be made biodegradable as a result of encapsulation or inclusion into degradable drug delivery vehicles or carriers, e.g. polymeric matrices, particles or membrane vesicles (liposomes). These delivery systems are usually either implantable or injectable. Implantable drug delivery systems are often placed under the epidermis where the components of the system are usually slowly degraded as a result of biological activity of surrounding cells (i.e. as a result of the release of enzymes degrading chemical bonds that hold these implants together).

Polylysine and other polyamino acids have previously been modified by the attachment of phospholipid groups and used in DNA transfection (Zhou, X H et al (1991) Biochem. Biophys. Acta 1065: 8-14 and Zhou, X h, Huang L (1994) Biochem. Biophys Acta 1189: 195-203). Polylysine has also been modified by the attachment of hydrophilic groups such as polyethylene glycol, a protective group (Dash P R, et al (1997) J. Contr. Rel. 48: 269-276), and various sugars (Kollen W J W, et al, (1996) Human Gene Ther. 13: 1577-1586 and Erbacher P, et al (1997) Biochimica Biophysica Acta 1324: 27-36) but no distinct hydrophobic moiety. Additionally, various drugs (Hudecz F. et al (1993) Bioconjugate chemistry 4: 25-33) and targeting residues such as transferrin (Wagner, E (1994) Adv. Drug Delivery Rev. 14: 113-135), asialoglycoprotein (Chowdhury, N R et al (1993) J. Biol. Chem. 268: 11265-11271) and monoclonal antibodies (Chen, J B et al (1994) Febs Lett 338: 167-169) have been conjugated to polylysine.

U.S. Pat. No. 5,871,710 to Bogdanov et al. discloses a biocompatible graft co-polymer adduct including a polymeric carrier, a protective chain linked to the polymeric carrier, a reporter group linked to the carrier or to the carrier and protective chain, and a reversibly linked Pt(II) compound for diagnosis.

U.S. Pat. No. 7,138,105 to Bolotin discloses a biocompatible graft co-polymer comprising of a metal bridge flanked by two metal binding molecules wherein one of the metal binding molecules is part of, or covalently linked to, the therapeutic agent. The bridge links the carrier and therapeutic agent capable of binding U.S. Pat. No. 6,576,254 to Uchegbu discloses polyamino acid vesicles comprising of polylysine grafted with MPEG, fatty acids and cholesterol.

SUMMARY OF THE INVENTION

The present invention is directed towards novel drug delivery systems and methods of making and using the same. It is an object of the present invention to provide a delivery system for a therapeutic agent that has a sustained release capability, is safe, biocompatible, readily prepared from known chemistries and compounds, whose release rate can be readily adjusted by simple mechanisms, and is amenable to a wide variety of therapeutic agents such as peptides, proteins and other hydrophobic drugs. The invention provides a novel protected graft co-polymeric carrier with a linear polymeric backbone made up of repeating units (called residues), preferably between 30 to 500 residues, with modifiable functional groups (such as amino, carboxyl, hydroxyl, sulfur, and phosphate), modified in such a way to contain at least one hydrophobic moiety and a plurality of hydrophilic protective groups pendant to the polymeric backbone in a weight ratio that renders the composition soluble in water and size that allows for subcutaneous delivery. The large number of protective groups acts as a shield to protect load molecules from being exposed to the surface of the carrier prior to release by dissociation.

The invention provides means to deliver hydrophobic peptides, hydrophobic proteins and hydrophobic drugs in patients in a controlled manner without the use of vesicles. Controlled manner means that the level of the active therapeutic molecules in the circulation will neither exceed a toxic level nor drop below the therapeutically effective level for the desired period of time (see FIG. 7). The ability of the carrier of the present invention to release free and active therapeutic agent, or in a broader sense, a "load molecule", when the level of free load molecule in the circulation goes below the therapeutically effective level may be readily adjusted. The carriers of the present invention may be prepared to have both high loading capacity and adjustable release rates by controlling the length, number and density of hydrophobic moieties in which alkyl chains are more commonly used. Release rate can also be controlled by the size of the carrier. The carriers of the present invention are safe and non-immunogenic due to the presence of multiple non-immunogenic protective chains that shield the more immunogenic core of the carrier.

In one aspect this invention provides a soluble hydrophobic-core carrier composition comprising: (i) a linear polymeric backbone; (ii) a plurality of hydrophilic polymeric protective chains covalently linked and pendant to the polymeric backbone, wherein each protective side chain has a molecular weight between about 400 and about 20,000 Daltons; and (iii) at least one hydrophobic moiety covalently linked and pendant to the polymeric backbone; wherein the weight ratio of the hydrophilic polymeric protective side chains and the hydrophobic moieties is selected so that the composition is soluble in water. In one embodiment the weight ratio of the hydrophilic polymeric protective side chains and the hydrophobic moieties is at least 15:1, at least 17:1, at least 20:1, at least 50:1 or at least 100:1. (See Table 2). In another embodiment at least 90% of the residues of the polymeric backbone are derivatized with either hydrophilic protective chains or hydrophobic moieties. In another embodiment the protective side chains comprise polyethylene glycol, polypropylene glycol, a co-polymer of polyethylene glycol, a co-polymer of polypropylene glycol, polysaccharide, or alkoxy derivatives thereof. In another embodiment the alkoxy derivative is methoxypolyethylene glycol, methoxypolypropylene glycol, a methoxylated co-polymer polyethylene glycol and polypropyleneglycol, or ethoxylated polysaccharide. In another embodiment the linear polymeric backbone is selected from a group consisting of polylysine, polyaspartic acid, polyglutamic acid, polyserine, polythreonine, polycysteine, polyglycerol, natural saccharides, aminated polysaccharides, aminated oligosaccharides, polyamidoamine, polyacrylic acids, polyalcohols, sulfonated polysaccharides, sulfonated oligosaccharides, carboxylated polysaccharides, carboxylated oligosaccharides, aminocarboxylated polysaccharides, aminocarboxylated oligosaccharides, carboxymethylated polysaccharides, and carboxymethylated oligosaccharides.

In another aspect, this invention provides the aforementioned soluble hydrophobic-core carrier composition and further comprises a load molecule dissociably linked to the hydrophobic moiety of the backbone. In one embodiment the hydrophilic protective side chains comprise methoxypolyethylene glycol. In another embodiment the hydrophilic protective side chains comprise methoxypolyethylene glycol and the polymeric backbone comprises polylysine. In another embodiment the hydrophilic protective side chains comprise methoxypolyethylene glycol, the polymeric backbone comprises polylysine and the hydrophobic moieties comprise a fatty acid. In another embodiment the hydrophilic protective side chains comprise methoxypolyethylene glycol, the polymeric backbone comprises polylysine, the hydrophobic moieties comprise a fatty acid and the load molecule is a therapeutic agent. In one embodiment, the therapeutic agent is a hydrophobic peptide, hydrophobic protein, or a hydrophobic drug. In another embodiment the therapeutic agent is GLP-1.

In another embodiment, the therapeutic agent is selected from GLP-2, leptin, islet amyloid polypeptide and vasoactive intestinal peptide.

In another aspect, this invention provides the aforementioned soluble hydrophobic-core carrier composition comprising a load molecule dissociably linked to the hydrophobic moiety of the backbone where the linear polymeric backbone is polylysine. In one embodiment the hydrophobic moiety(ies) comprises a fatty acid selected from the range of 6-carbon fatty acids to 36-carbon fatty acids. In another embodiment the hydrophobic moiety(ies) comprise a fatty acid with at least one double bond. In another embodiment the hydrophobic moiety(ies) comprises a multi-fatty acid-containing moiety. In another embodiment the hydrophobic moiety(ies) comprises an aromatic ring containing moiety.

In some embodiments the carrier may optionally include a second protective chains covalently linked to the hydrophobic moiety for enhancing solubility or maintaining the hydrophilic protective chains to hydrophobic moieties weight ratio above 15:1, thus preventing vesicle formation and precipitation.

In various embodiments, the load molecule may be a therapeutic agent or an imaging agent. In one embodiment the therapeutic agent is a hydrophobic peptide, hydrophobic protein, or a hydrophobic drug. In another embodiment, the therapeutic agent can be GLP-2, leptin, islet amyloid polypeptide (IAPP, also known as amylin) and vasoactive intestinal peptide (VIP). In one embodiment, the therapeutic agent may be hydrophobic polynucleotide, hydrophobic peptide, hydrophobic protein, or hydrophobic drugs. The hydrophobic peptide/protein may be peptide aptamer, glucagon-like-peptide, glucagon-like-peptide derivative, exenatide, leptin, leptin fragment, Peptide YY, alpha-melanocyte stimulating hormone, adiponectin, obestatin, Gastric inhibitory polypeptide (GIP), Epidermal Growth Factor (EGF) receptor ligand, EGF, Transforming Growth Factor alpha (TGF-alpha), Betacellulin, Gastrin/Cholecystokinin receptor ligand, Gastrin, Cholecystokinin, interferon, interferon gamma, interferon beta, interferon alpha, interleukin-1, interleukin-2, interleukin-4, interleukin-6, interleukin-8, interleukin-10, interleukin-12, tumor necrosis factor, tumor necrosis factor alpha, tumor necrosis factor beta, insulin, insulin-like growth factor, growth hormone, nerve growth factor, brain-derived neurotrophic factor, enzymes, endostatin, angiostatin, trombospondin, urokinase, streptokinase, blood clotting factor VII, blood clotting factor VIII, granulucyte-macrophage colony-stimulating factor (GM-CSF), granulucyte colony-stimulating factor (G-CSF), thrombopoetin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastin, terlipressin, and vasoactive intestinal peptide (VIP).

In further embodiment the present invention relates to all the aforementioned compositions further comprising of targeting moiety covalently linked to the distal end of the protective group. The targeting moiety may be an antibody, fragment of an antibody, chimeric antibody, lectins, receptor ligands, proteins, enzymes, peptides, saccharides, quasi substrates of enzymes, cell-surface-binding compounds, and extracellular-matrix-binding compounds.

In another aspect, this invention provides a pharmaceutical composition comprising any one composition selected from the compositions above wherein the load molecule is a therapeutic agent.

In another aspect, this invention provides a method of making a composition comprising: (a) dissolving a polymeric backbone containing residues comprising free amino groups in an aqueous buffer of pH 7-8 to obtain solution A; (b) activating a carboxyl group or alkyl carboxyl group of a protective chain by mixing it with a carbodiimide reagent in acidic buffer between pH 3-7 to obtain solution B; and (c) adding solution B to solution A resulting in a solution C with a pH of 7 or above, containing a polymeric backbone with covalently linked protective chains.

In another aspect, this invention provides a method of making a composition comprising: (a) dissolving in non-aqueous solvent with a tertiary amine, a component comprising a polymeric backbone covalently linked to protective chains, wherein the polymeric backbone comprises residues comprising free amino groups, thereby obtaining solution E; (b) dissolving in a non-aqueous solvent hydrophobic molecules containing free carboxyl groups and activating the carboxyl groups by adding carbodiimide reagent to obtain solution F; and (c) adding solution F to solution E to obtain solution G to form covalent linkage between the activated carboxyl groups and the free amine groups; wherein solution E is added to solution G until at least 90% of the residues are linked to protective chains or hydrophobic groups.

In another aspect, this invention provides a method of making a composition comprising: (a) dissolving in partially-aqueous solvent at pH of 7 to 9 a component comprising a polymeric backbone covalently linked to protective chains, wherein the polymeric backbone comprises residues comprising free amino groups, thereby obtaining solution E, (b) dissolving in partially-aqueous solvent with pH of 3 to 7, hydrophobic molecules containing free carboxyl groups and activating the carboxyl groups by adding carbodiimide reagent resulting in solution F, (c) adding solution F to solution E while maintaining the pH of the mixture between 7-8 to obtain solution G, to form covalent linkage between the activated carboxyl groups and the free amine groups; wherein solution E is added to solution G until at least 90% of the residues are linked to protective chains or hydrophobic groups.

In another aspect, this invention provides a method of loading a composition comprising: a) dissolving in aqueous or partially-aqueous solvent A soluble hydrophobic-core carrier composition comprising: (i) a linear polymeric backbone; (ii) a plurality of hydrophilic polymeric protective chains covalently linked and pendant to the polymeric backbone, wherein each protective side chain has a molecular weight between about 400 and about 20,000 Daltons; and (iii) at least one hydrophobic moiety covalently linked and pendant to the polymeric backbone; wherein the weight ratio of the hydrophilic polymeric protective side chains and the hydrophobic moieties is selected so that the composition is soluble in water, thereby obtaining solution A. (b) dissolving the load molecule in aqueous or partially-aqueous solvent to obtain solution B, (c) mixing solution A with solution B to obtain solution C, incubating solution C for 30 minutes or longer followed by lyophilization or solvent evaporation to obtain a loaded carrier ready to be dissolved into appropriate solvent.

In another aspect, this invention provides a method of administering a therapeutic molecule to a subject comprising administering to the subject a composition comprising: (i) a linear polymeric backbone; (ii) a plurality of hydrophilic polymeric protective chains covalently linked and pendant to the polymeric backbone, wherein each protective side chain has a molecular weight between about 400 and about 20,000 Daltons; (iii) at least one hydrophobic moiety covalently linked and pendant to the polymeric backbone; (iv) a therapeutic molecule dissociably linked to the hydrophobic moiety of the backbone; wherein the weight ratio of the hydrophilic polymeric protective side chains and the hydrophobic moieties is selected so that the composition is soluble in water. In one embodiment, the composition is administered subcutaneously or intramuscularly.

In another aspect this invention provides a pharmaceutical composition comprising: (a) a composition comprising: (i) a linear polymeric backbone; (ii) a plurality of hydrophilic polymeric protective chains covalently linked and pendant to the polymeric backbone, wherein each protective side chain has a molecular weight between about 400 and about 20,000 Daltons; (iii) at least one hydrophobic moiety covalently linked and pendant to the polymeric backbone; (iv) a therapeutic molecule dissociably linked to the hydrophobic moiety of the backbone; wherein the weight ratio of the hydrophilic polymeric protective side chains and the hydrophobic moieties is selected so that the composition is soluble in water; and (b) a pharmaceutically acceptable carrier; wherein the composition is in unit dose form.

DETAILED DESCRIPTION OF THE INVENTION

Definitions

Figure 1:
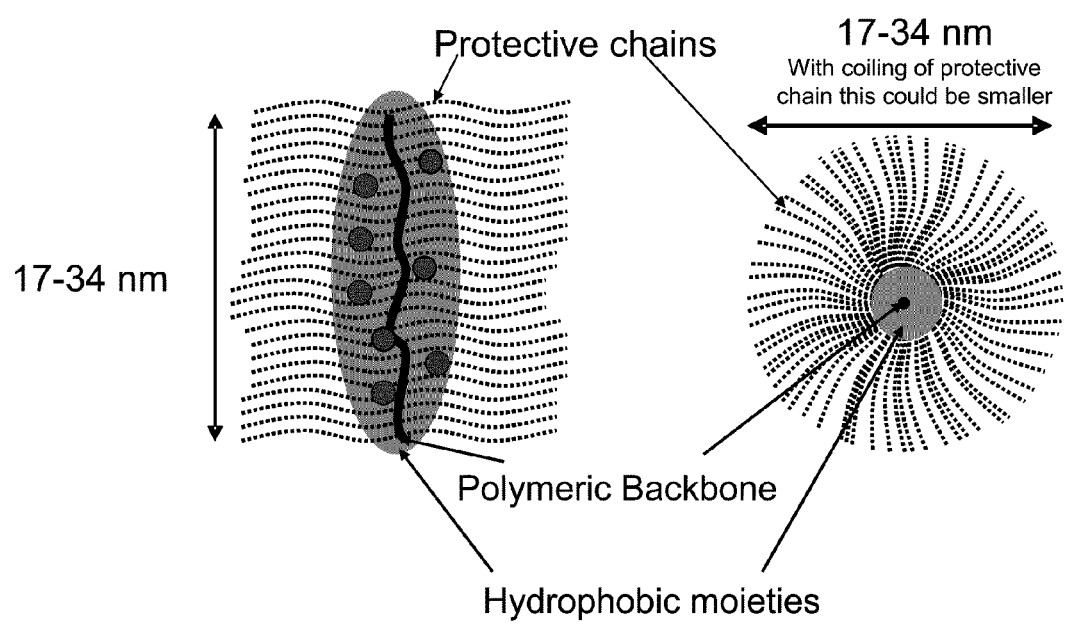
FIG. 1 depicts a schematic representation of one embodiment of the hydrophobic-core composition of the invention: a linear polymeric backbone; protective side chains covalently linked to polymeric backbone; hydrophobic moieties covalently linked to polymeric core, and hydrophobic load molecule with diameter of 3 nm. The dimension of the carrier is also shown to emphasize that it is greater than the 4 nm glomerular filtration cut off, whereas carrier and hydrophobic load molecules together are below this cut off. The followings are example of proteins and their diameter: siRNA (diameter<3 nm), albumin hydrated (diameter=7.2 nm); growth hormone hydrated (diameter=3 nm); glomerular filtration diameter <4 nm; beta-2 macroglobulin (diameter=3.2 nm); myoglobin (diameter=3.9 nm); hemoglobin (diameter=6.5 nm); gamma globulin (diameter=11.1 nm); and Bence-Jones protein (diameter=5.5 nm).

For convenience, before further description of the present invention, certain terms employed in the specification, examples and appended claims are collected here. These definitions should be read in light of the remainder of the disclosure and understood as by a person of ordinary skill in the art. Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "a protective chain" means one protective chain or more than one protective chain.

The term "aptamer" means oligonucleic acid or peptide molecules that bind a specific target molecule through specific folding. One of the embodiments of the present invention is to deliver hydrophobic peptide aptamers by providing carrier with hydrophobic moiety. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. Aptamers offer the utility for biotechnological and therapeutic applications as they offer molecular recognition properties that rival that of the commonly used biomolecule, antibodies. This is possible through specific folding to create recognition sites. Although this folding can be interrupted by binding to the carrier, upon release from the carrier re-folding will occur to provide aptamers that has the right folding to be biologically or therapeutically active. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Aptamers are cleared rapidly from the bloodstream, with a half-life of minutes to hours, mainly due to degradation and clearance from the body by the kidneys, a result of the aptamer's inherently low molecular weight. Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which has good solubility (which for the purpose of the present invention will preferably hydrophobic) and compact properties. These peptide aptamers can be made to contain fatty acids to increase hydrophobicity to be able to load into the present invention by hydrophobic interaction. While the aptamer is loaded into the carrier of the present invention it is protected from degradation due to high density of protective chain shielding The term "derivative" or "analog" as used herein refers to a compound whose core structure is the same or closely resembles that of, a parent compound, but which has a chemical or physical modification, such as different or additional groups. The term also includes a peptide with at least 50% sequence identity (i.e. amino acid substitution is less than 50%) with the parent peptide. The term also includes a peptide with additional groups attached to it compared to the parent peptide, such as fatty acids and/or additional amino acids that do not exceed the mass of the original parent peptide. The term also includes a polymer with additional group attached to it, such as, in the case of a protective group, an alkoxy group, compared to the parent polymer. The term also includes methoxylated or ethoxylated protective chains with additional methoxy- or ethoxy-group(s) attached to it compared to the parent protective chains.

The term "hydrophobic moiety" as used herein refers to a molecule or molecular moiety attached to the backbone that is non-polar and provides a hydrophobic environment for the load molecule to interact in order to avoid the surrounding water environment. Hydrophobic moieties may be aliphatic hydrocarbon chains and/or ring compounds that do not have positive or negative charge and are capable of binding to molecules by hydrophobic interaction. The hydrophobic moieties are the portions of the molecule that are typically made up of hydrogen and carbon with minimal amount of oxygen and nitrogen. The hydrophobic moiety can be a single continuous portion of a molecule having six or more carbons linked together where the total number of nitrogen plus oxygen bonded to this portion is one third or less than of the number of carbon atoms. It is also understood that the hydrophobic moiety counts as a separate entity from the polymeric backbone, such that, for example, when the polymeric backbone is a polyamino acid, the natural R group on the polyamino acid is not counted as a hydrophobic moiety in the present invention. For example, a hydrophobic moiety may be added to a polylysine backbone through amide formation from amine group.

The term "load molecule" as used herein encompasses any molecule that binds with high affinity (those with affinity constant (Ka) of greater than 0.01 million/molar or dissociation constant (Kd) of less than 100 micromolar) to the carrier, allowing it to be loaded into the carrier. The affinity constant or dissociation constant can easily be ascertained by those skilled in the art. For the purpose of the present invention, these load molecules include hydrophobic peptides (50 or less amino acids), hydrophobic proteins (greater than 50 amino acids), polynucleotide (RNA, DNA or their analogs) with additional hydrophobic moieties or with additional agent that neutralize the negatively charged polyphosphate backbone, and other hydrophobic molecules.

The term "non-proteinaceous polyamino acid" as used herein refers to a polyaminoacid that is not naturally made by a living organism unless recombinantly engineered by human. Non-limiting examples of these are poly-(L and/or D)-lysine, poly-(L and/or D)-glutamate, poly-(L and/or D)-glutamate, poly-(L and/or D)-aspartate, poly-(L and/or D)-serine, poly-(L and/or D)-threonine, poly-(L and/or D)-tyrosine, and poly-(L and/or D)-arginine. The non-proteinaceous polyamino acid also includes polyamino acids with R-groups that are not naturally occurring but contains carboxyl, amino, hydroxyl, or thiol groups that can provide repeating functional groups (from 30 to 1000 functional groups) that are modifiable for the attachment of protective groups and/or oligonucleotides. The non-proteinaceous polyaminoacids are among the possible backbone component of the invention.

The term "hydrophilic protective side chain" as used herein refers to a molecule(s) which protects the carrier-core and the load molecule from contact with other macromolecules due to extensive linking or binding of water to the chains. Because of this extensive binding with water molecules the protective chain also increases water solubility of the composition. The protective group does not have significant amount of charge but is water soluble. Generally, the groups are non-immunogenic. This also means that protective chain provides hydrophilic property to the composition. The term "protective side chain" is used interchangeably with the terms "protective group" and "protective chain". The protective chains of the present composition include polyoxyethylene glycol also referred to as polyethylene glycol and their derivatives. The protective chains of the present composition also include uncharged polysaccharides and their derivatives such as ethoxylated or methoxylated polysaccharides. In this context, uncharged means that the main body of the chain does not have positive or negative charge.

The term "targeting moiety," "targeting molecules," or "targeting group" refers to any molecular structure which assists the construct of the composition in localizing at a particular target area, entering a target cell(s), and/or binding to a target receptor. For example, lipids (including hydrophobic, neutral, and steroidal lipids), antibodies, antibody fragments, chimeric antibodies, lectins, ligands, receptor ligands, sugars, saccharides, steroids, hormones, nutrients, peptides, proteins, enzymes, quasi substrates of enzymes, cell-surface-binding compounds, and extracellular-matrix-binding compounds may serve as targeting moieties. Targeting moieties are preferably attached to the distal portion of protective chains of the carrier.

The term "therapeutic agents" as used herein refer to any chemical that is a biologically, physiologically, or pharmacologically active and act locally or systemically in a subject. For the purpose of the present invention, therapeutic agent loaded into the carrier is understood to be hydrophobic such as hydrophobic peptides and proteins or to have hydrophobic moiety modification such as fatty acids or phenyl ring. Examples of therapeutic agents (also referred to as "drugs") which has significant hydrophobic moieties or may be enhanced to have significant hydrophobic moieties by covalently linking it into fatty acids includes glucagon-like-peptide, glucagon-like-peptide derivatives, exenatide, glucagon-like-peptide-1, glucagon-like-peptide-2, leptin fragment, Gastric inhibitory polypeptide (GIP), Epidermal Growth Factor (EGF) receptor ligand, EGF, Transforming Growth Factor alpha (TGF-alpha), Betacellulin, Gastrin/Cholecystokinin receptor ligand, Gastrin, Cholecystokinin, lysostaphin, interferon, interferon gamma, interferon beta, interferon alpha, interleukin-1, interleukin-2, interleukin-4, interleukin-6, interleukin-8, interleukin-10, interleukin-12, auristatin, nisin, insulin, insulin-like growth factor 1, growth hormone, growth hormone releasing hormone (GHRH), nerve growth factor, brain-derived neurotrophic factor, enzymes, endostatin, angiostatin, trombospondin, urokinase, streptokinase, blood clotting factor VII, blood clotting factor VIII, granulucyte-macrophage colony-stimulating factor (GM-CSF), granulucyte colony-stimulating factor (G-CSF), thrombopoetin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastin, prostaglandins, epoprostenol, prostacyclin, cyclosporine, vasopressin, terlipressin, desmopressin, cromolyn sodium (sodium or disodium chromoglycate), and vasoactive intestinal peptide (VIP). Any hydrophobic molecules may be attached to the above therapeutic agents to facilitate loading or improve their affinity to the carrier. The hydrophobic moieties attached to the therapeutic agent can be any fatty acids or their analogs. The therapeutic agents may be natural hydrophobic peptides that are non-immunogenic but are susceptible to breakdown and elimination without the protection of the carrier.

The term "therapeutically effective amount" as used herein refers to the amount of composition that will provide a therapeutic benefit to the patient. In certain embodiments, the term refers to an amount of the therapeutic agent that, when loaded to the hydrophobic core carrier composition of the present invention and administered to the patient, produces some desired effect at a reasonable benefit/risk ratio applicable to any medical treatment. The effective amount may vary depending on such factors as the disease or condition being treated, the particular constructs being administered, the size of the subject and/or the severity of the disease or condition. One of ordinary skill in the art may empirically determine the therapeutically effective amount of a particular compound without necessitating undue experimentation. In certain embodiments, the term refers to that amount necessary or sufficient for a use of the subject compositions described herein. In the treatment of obesity, the therapeutically effective amount is the amount of composition of the present invention with corresponding load molecule(s) such as, but not limited to, leptin that will reduce appetite and/or weight. In the treatment of obesity, the therapeutically effective amount is the amount of composition of the present invention with corresponding load molecule(s) such as, but not limited to, PYY, hat will reduce appetite and/or weight. In the treatment of insulin-insufficient diabetes, the therapeutically effective amount is the amount of composition of the present invention with corresponding load molecule(s) that will improve glucose homeostasis or normalize blood glucose level of the patient and/or regenerate the beta-islet cells in the pancreas. The regeneration of the beta-islet cells the can be indirectly measured by monitoring blood glucose level, Hemoglobin A1c level, C-peptide level, or insulin level in the blood.

Descriptions of the Components of the Invention

This invention provides soluble compositions comprising a linear polymeric backbone or carrier with hydrophilic side chains and hydrophobic side chains appended thereto. Such compositions are useful, among other things, as carriers of hydrophobic molecules, such as therapeutic molecules. The hydrophobic molecules are affinity-bound to the hydrophobic side chains. Upon administration to a subject the composition is soluble and it releases the hydrophobic load molecule as a function of the kinetics of binding and local concentration. The compositions of the present invention have a weight ratio of hydrophilic side chains to hydrophobic side chains that renders the composition soluble in water, i.e., the composition is soluble in water at a concentration of 50 mg/ml and does not precipitate or render the solution cloudy. Generally, the weight ratio of hydrophilic side chains to hydrophobic side chains is at least 15:1. In various embodiments the weight ratio is above 17:1, above 20:1, above 25:1, above 50:1 or above 100:1. In other embodiments, the weight ratio is between 15:1 and 60:1; between 20:1 and 45:1 or between 25:1 and 40:1.

Example 8 shows solubility of compositions of varying length of polylysine and different ratios of MPEG to fatty acid. At MPEG:fatty acid ratios above 14:1, the compositions are soluble at a concentration of 50 mg/ml. At ratios between 10.5:1 and 13.7:1 the compositions are "partially soluble."

In certain embodiments, the composition of the present invention is made up of at least four components; a) a linear polymeric backbone, b) several hydrophilic protective chains covalently linked to the polymeric backbone and/or to the hydrophobic moiety c) several hydrophobic moieties covalently linked and pendant (linked to side of the backbone) to the linear polymeric back bone, and d) hydrophobic load molecules such as hydrophobic peptides (50 amino acids and less), hydrophobic proteins (over 50 amino acids), or hydrophobic drugs dissociably linked to the hydrophobic moieties. The preferable hydrophobic peptides, proteins and hydrophobic molecules have retention times greater than two minutes in one of their conformational states under the following HPLC conditions; A reversed phase HPLC column (SynergiMaxRP; 2.5 um, 4×20 mm; Phenomenex) eluted at a flow rate of 1.5 ml/min using a gradient of solvent A to B (25-50% B from 1-5 minutes) where A is water with 0.1% Trifluoroacetic acid (TFA)/5% Acetonitrile and solvent B is Acetonitrile with 0.1% TFA. The retention time of GLP-1 under this condition is 2.56 minute, VIP is 1.63 minute but small amount in the alpha conformation is 2.56 minutes, and leptin is 4.9 minutes. VIP is believed to assume more hydrophobic alpha conformation when exposed to the carrier resulting in more binding than expected (see Table 2, below). Other peptides and proteins that are not highly hydrophobic can be made hydrophobic by attaching fatty acids and the process of such modification is very well known in the art. The protective chain in the present invention is essential to hide the load molecules from degradation by enzymes and cells.

Polymeric Backbone

The polymeric backbone is a non-proteinaceous homo- or heteropolymer with repeating amino or carboxyl groups and may be of natural or synthetic origin. Preferably the polymeric backbone is polyamino acid which may have D- or L-chirality or both and more preferably a straight chain homopolymer. Preferred straight chain homopolymers include polylysine and polyornithine, polyarginine, polyglutamate, polyaspartate, polyserine, polythreonine, polytyrosine or any other amide linked hemoropolymer made from amino acids. A linear polyethylenimine may also be used a polymeric backbone. If the polymeric backbone is a polyamino acid, non-proteinaceous is preferable, meaning that it is not a protein made by living organism to have a three dimensional conformation associated activity. The polymeric backbone may have a molecular weight of about 600-1,000,000, preferably 3,000-100,000. It is also preferable to have 30 to 1000 modifiable functional groups. Other polymeric backbone with repeating modifiable functional groups may also be used such as those with repeating sulfhyryl(thiol), phosphate, and hydroxyl groups. Carbohydrate polymers and other synthetic polymers where monomers are non-biological may also be used as polymeric backbone. The polymeric backbone provides the multiple sites from where the hydrophobic chains and hydrophilic protective chains can be attached. In certain embodiments, at least 80%, at least 90%, at least 95% or at least 99% of the residues of the polymeric backbone are derivatized with hydrophilic or hydrophobic side chains.

Hydrophobic Moiety

The hydrophobic moieties may comprise hydrophobic alkyl groups, which have a general formula [CxHyOz] where x is 6-36; y is 2-71; z is 1-4. It is preferable that z=1, which is the minimum required for amide bond formation with the amino group of the polymeric backbone. The starting molecules (prior to attachment to polymeric backbone) however, may have z greater than 1 prior to amide bond formation. The hydrophobic moieties may also comprise two ended hydrophobic alkyl groups (one end attached to polymeric backbone) which have a general formula [—OC(CH$_2$)$_x$CO—] or [—OC(CH$_2$)$_x$CN—] where x is 6-36, and may further comprise protective groups covalently attached to the first end of the hydrophobic moieties and the second end covalently attached to the polymeric backbone.

In one embodiment, the chemical link of hydrophobic moieties to the polymeric backbone comprises amide bond. In another embodiment, the chemical link of hydrophobic moieties to the polymeric backbone comprises ether bond. In another embodiment, the chemical link of hydrophobic moieties to the polymeric backbone comprises ester bond. In another embodiment, the chemical link of hydrophobic moieties to the polymeric backbone comprises disulfide bond. In one embodiment, the hydrophobic moiety attached to polymeric backbone comprises an alkyl acyl derived from fatty acids, or aromatic alkyl acyl derived from aromatic alkyl acids, which has a general formula [CxHyOz] where x is 6-36; y is 2-71; z is 1-4. It is preferable that z=1, the starting molecules however may have z greater than 1 prior to bond formation with polymeric backbone.

Protective Hydrophilic Group or Protective Chains

Preferably the "protective hydrophilic group" or "protective chain" is non-ionic with a molecular weight of about 2000-20,000, preferably 5,000-10,000. The protective chain of the composition is preferably a polymer of ethylene oxide (or polyethyleneglycol also called polyoxyethyleneglycol), i.e. PEG or a mono-methoxy ether of polyethyleneglycol (i.e. MPEG). A protective chain is useful because: 1) it ensures the solubility the composition while maintaining a high drug payload, 2) a protective chain assists in the formation of a stearic barrier which can prevent load molecules (hydrophobic peptides, hydrophobic proteins and other hydrophobic therapeutic agents) from binding or interacting with other macromolecules, enzymes (nucleases and proteases) and cells in the body; 3) a protective chain provides load molecules (hydrophobic peptides, hydrophobic proteins and hydrophobic drugs) with long circulation times or biological half-lives in vivo (e.g. for decreasing glomerular filtration in kidneys, decreasing kidney and liver uptake, decreasing macrophage uptake) and creates a circulating depot; 4) a protective chain decreases undesirable immunogenicity of the carrier or its load molecules such as hydrophobic peptides and hydrophobic proteins and hydrophobic drugs; and 5) the protective chains increases the size of the carrier to take advantage of abnormal permeability of tumor vessels and assists accumulation of the carrier with load molecules in a tumor or inflammation site and delivering the load molecules or anti tumor compounds to the tumor which is especially useful for treating tumors and other highly vascularized areas of the body.

The protective chain of the hydrophobic core carrier composition may be polyethylene glycol, polypropylene glycol, methoxypolyethylene glycol, methoxypolypropylene glycol, a co-polymer of polyethylene glycol and polypropylene glycol; or a alkoxy derivative thereof. It is preferable that the protective chain is one of methoxypolyethylene glycol, methoxypolypropylene glycol, or a co-polymer of methoxypolyethylene glycol and methoxypolypropyleneglycol. The protective chain may also be polyethylene glycol monoamine, methoxypolyethylene glycol monoamine, methoxy polyethylene glycol hydrazine, methoxy polyethylene glycol imidazolide or a polyethylene glycol diacid. Protective chains are linked to the polymeric backbone and/or hydrophobic moieties pendant to the polymeric backbone preferably by a single linkage. Methoxylated or ethoxylated polysaccharides can also be used as protective chains in the present invention since alkoxylation will reduce or eliminate their immunogenicity and will thus act as improved protective chains.

Hydrophobic Load Molecules

The hydrophobic load molecules are preferably hydrophobic peptides and proteins; lipids, and hydrophobic drugs. Among these includes hydrophobic imaging agent and hydrophobic therapeutic agent. Hydrophobic peptides and proteins include cytokine, lymphokine, hormone, and enzymes.

The load molecules of the present invention also include therapeutic agents derivatized to contain hydrophobic moieties or naturally hydrophobic therapeutic agent. These includes siRNA, antisense-DNA, antisense-RNA, glucagon-like-peptide, glucagon-like-peptide derivatives, exenatide, glucagon-like-peptide-1, glucagon-like-peptide-2, leptin, leptin fragment, Gastric inhibitory polypeptide (GIP), Epidermal Growth Factor (EGF) receptor ligand, EGF, Transforming Growth Factor alpha (TGF-alpha), Betacellulin, Gastrin/Cholecystokinin receptor ligand, Gastrin, Cholecystokinin, lysostaphin, interferon, interferon gamma, interferon beta, interferon alpha, interleukin-1, interleukin-2, interleukin-4, interleukin-6, interleukin-8, interleukin-10, interleukin-12, tumor necrosis factor, tumor necrosis factor alpha, tumor necrosis factor beta, auristatin, nisin, insulin, insulin-like growth factor, growth hormone, growth hormone releasing hormone (GHRH), nerve growth factor, brain-derived neurotrophic factor, enzymes, endostatin, angiostatin, trombospondin, urokinase, streptokinase, blood clotting factor VII, blood clotting factor VIII, granulucyte-macrophage colony-stimulating factor (GM-CSF), granulucyte colony-stimulating factor (G-CSF), thrombopoetin, calcitonin, parathyroid hormone (PTH) and its fragments, erythropoietin, atrial natriuretic factor, monoclonal antibodies, monoclonal antibody fragments, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastin, prostaglandins, epoprostenol, prostacyclin, cyclosporine, vasopressin, terlipressin, desmopressin, cromolyn sodium (sodium or disodium chromoglycate), vasoactive intestinal peptide (VIP), vancomycin, antimicrobials, polymyxin b, anti-fungal agents, anti-viral agents, enfuvirtide, doxorubicin, etoposide, fentanyl, ketamine, and vitamins. The preferred hydrophobic moieties to attached therapeutic peptides and proteins to increase their hydrophobicity are fatty acids from 6 to 36 carbon units, with the intention of facilitating loading into the carrier during the formulation.

Chemical Assembly of the Carrier from Individual Components

Attaching Protective Chains to Amino Groups of the Polymeric Backbone:

The present invention relates to a polymeric backbone further comprising a protective chains and hydrophobic moiety. The modification of the polymeric backbone containing amino groups is the amide covalent attachment of protective chains comprising methoxypolyethyleneglycol. A non-limiting example of an amino group modification along the polymeric backbone is attachment of protective chains comprising acyl methoxypolyoxyethyleneglycol (MPEG). An example of a protective chain with or without hydrophobic chain attached which is not intended to limit the scope of this invention is an acyl PEG, analog or derivative thereof which can be represented by formula: —CO(CH$_2$)$_n$COOCH$_2$CH$_2$-A-OR$_3$ or —COCH$_2$-A-OR$_3$, where n is 2-22 (representing hydrophobic moiety); A (representing protective chain) is [OCH2CH2]$_x$ or [OCH2CH2]$_x$ or [OCHCH$_3$CH$_2$]$_x$, where x is 17-500, or various combinations of [OCH2CH2], [OCH2CH2], and/or [OCHCH$_3$CH$_2$] with total of 17-500 units, R$_3$ is H, (CH$_2$)$_p$CH$_3$ or (CH$_2$)$_p$COOH, and p is 0-7.

Figure 2:
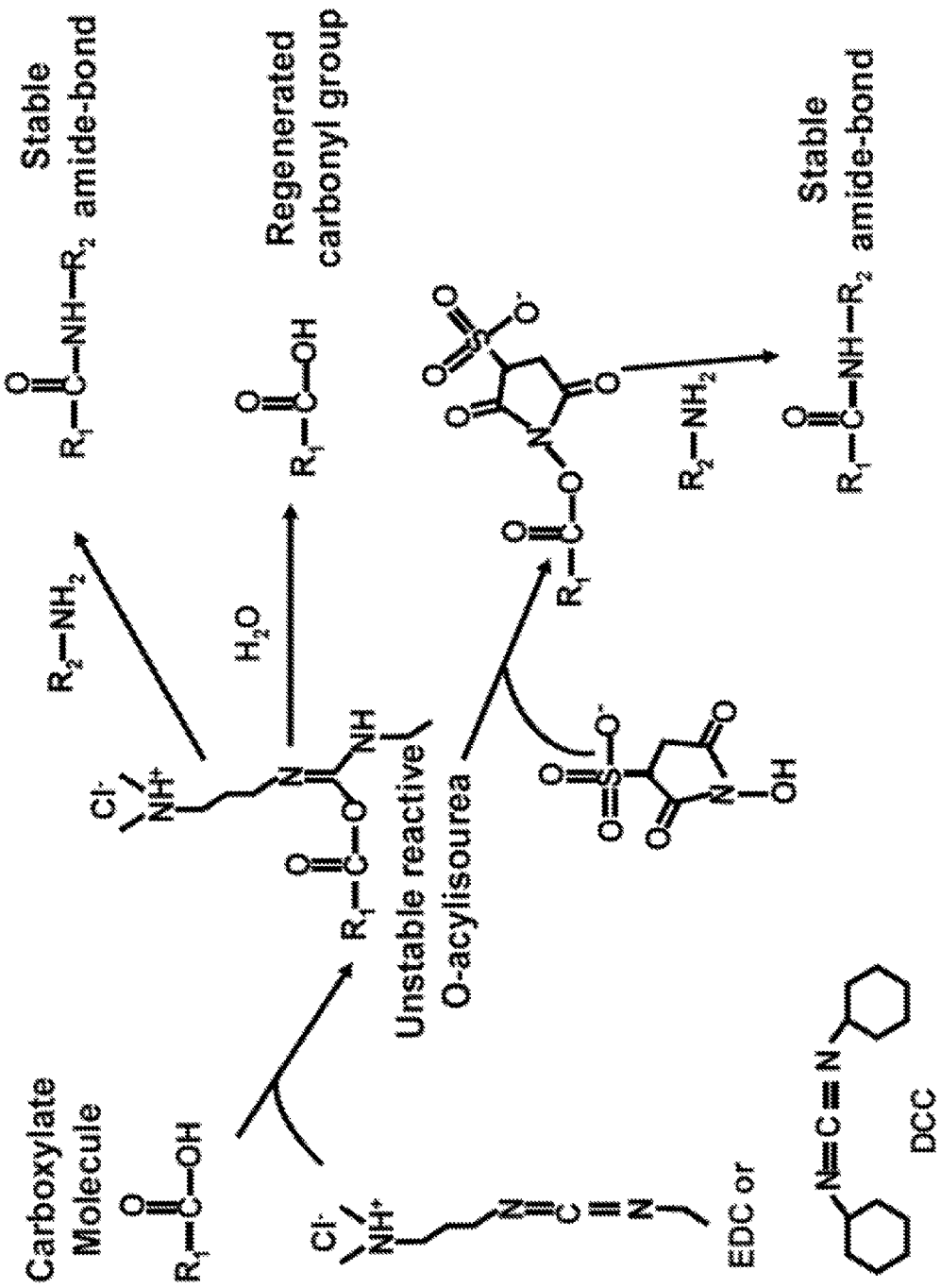
FIG. 2 depicts a diagram of various chemical reactions for making amide bonds that are useful in making the composition of the invention; $R_1$ can be hydrophobic molecule and $R_2$ can be polylysine, or polylysine-PEG; or $R_1$ can be PEG-carboxyl and $R_2$ can be polylysine, hydrophobic molecule-polylysine; or $R_1$ can be polyglutamate or polyaspartate and $R_2$ can be PEG-amine, hydrophobic molecule (such as alkyl amine from C6 to C36); or $R_1$ can be polyglutamate-PEG or polyaspartate-PEG and $R_2$ can be alkyl amine. EDC is a water soluble version of DCC; both can be used to carry out the reactions.

Another object of the present invention is to provide a method of attaching protective chains to the amino group containing polymeric backbone. The modifications can be done by amide bond formation. As an example that is not intended to limit the scope of this invention, the carboxyl containing protective chain can be attached to the amino group of the polymeric backbone using carbodiimide containing reagent such a 1-ethyl-3-(3-dimethylaminopropyl)-carbodiimide or dicyclohexylcarbodiimide (see FIG. 2). A carbodiimide reagent contains a functional group consisting of the formula N═C═N. During the process of coupling reaction, the activated carboxyl group O-acylisourea-intermediate can be stabilized by forming N-hydroxysuccinimide ester using N-hydroxysuccinimide. This relatively stable intermediate can react with the amino group of carrier such as polylysine or chitosan to form amino-acyl bond or amide bond. Similar result can also be accomplished by reacting aldehyde containing protective group to the amino group along the carrier. The aldehyde can react with the amino group of carrier such as polylysine or chitosan to form amino-acyl bond or amide bond.

Attaching Protective Chains to Carboxyl Groups of Polymeric Backbone:

The present invention relates to a polymeric backbone further comprising a protective chains and hydrophobic moiety. The modification of the polymeric backbone containing carboxyl groups is the amide covalent attachment of an amino group containing protective chains comprising amino methoxypolyoxyethyleneglycol (MPEG). As an example that is not intended to limit the scope of this invention, the protective chain with or without hydrophobic moiety can be an amino PEG which can be represented by formula $-NH(CH_2)_n NH\text{-}COCH_2\text{-}A\text{-}OR_3$, $-NH(CH_2)_n NHCO(CH_2)_n COOCH_2 CH_2\text{-}A\text{-}OR_3$, where n is 2-22 (representing the hydrophobic moiety); A (representing protective group) is $[OCH_2CH2]_x$ or $[OCH_2CH_2]_x$ or $[OCHCH_3CH_2]_x$, where x is 17-500, or various combinations of $[OCH_2CH_2]$, $[OCH_2CH_2]$, and/or $[OCHCH_3CH_2]$ with total of 17-500 units, $R_3$ is H, $(CH_2)_p CH_3$ or $(CH_2)_p COOH$, and p is 0-7.

Another object of the present invention is to provide methods of attaching protective chains to the polymeric backbone. These modifications can be done by amide bond formation. As an example that is not intended to limit the scope of this invention, the carboxyl group of the polymeric backbone can be activated to react with amino functional group of the protective chains (see FIG. 2). The activation can be accomplished using carbodiimide containing reagent such a 1-ethyl-3-(3-dimethylaminopropyl)-carbodiimide or dicyclohexylcarbodiimide. A carbodiimide reagent contains a functional group consisting of the formula $N=C=N$. During the process of activation the carboxyl group forms O-acylisourea-intermediate that can be stabilized by N-hydroxysuccinimide to form N-hydroxysuccinimide ester. This relatively stable intermediate can react with the amino group of protective molecules. If the protective group or molecule that needs to be introduced into the carrier does not have amino group, the amino group can be introduced to this molecule very easily and this process is well known to those skilled in the art.

Attaching Protective Chains to Hydroxyl Groups of Polymeric Backbone:

The present invention relates to a polymeric backbone further comprising protective chains and hydrophobic moiety. The modification of the polymeric backbone containing hydroxyl groups is the ester or ether bond formation with protective chains comprising methoxypolyethyleneglycol. The modification of hydroxyl groups of polymeric backbone is by ester bond formation with protective groups comprising acyl methoxypolyethyleneglycol. As an example that is not intended to limit the scope of this invention, the protective group can be a PEG with acyl or carbonyl represented by $-CO$ and attached to O of hydroxyl group of carrier to form ester. The acyl PEG with or without hydrophobic group or its derivative can be represented by formula $-CO(CH_2)_n NH\text{-}COCH_2\text{-}A\text{-}OR_3$, $-COCH_2CH_2\text{-}A\text{-}OR_3$, or $-COCH_2\text{-}A\text{-}OR_3$, where n is 2-22 (representing the hydrophobic moiety); A (representing protective group) is $[OCH_2CH_2]_x$ or $[OCH_2CH_2]_x$ or $[OCHCH_3CH_2]_x$, where x is 17-500, or various combinations of $[OCH_2CH_2]$, $[OCH_2CH_2]$, and/or $[OCHCH_3CH_2]$ with total of 17-500 units, $R_3$ is H, $(CH_2)_p CH_3$ or $(CH_2)_p COOH$, and p is 0-7.

The modification of hydroxyl group can be facilitated by synthesis of acyl halides of protective chains. Synthesis of acyl halides can be done by reaction of the carboxylic acid moiety of protective chains with dichlorosufoxide ($SOCl_2$) or other reagent known to those skilled in the art. The resulting acyl halides are reactive to alcohols including serine, threonine, and tyrosine residue of poly amino acids. The reaction will result in an ester bond formation essentially attaching the protective groups or molecules into the carrier. PEG-epoxide, PEG-isocyanate, PEG-PNC (PEG-nitrophenylcarboxyester) are the PEG analogs that may be used to modify the hydroxyl groups forming ether, ester, and urethane linkage respectively between protective group and the carrier.

Figure 3:
FIG. 3 depicts a diagram of various chemical reactions for attaching hydrophobic amine ($R^2$) to carrier ($R^1$) containing functional groups such as isothiocyanate, succinimidyl ester, or sulfonyl chloride. The carrier $R^1$ can be any backbone polymers. Polymer $R^1$ can be polyglutamate, polyaspartate, polyglutamate-PEG or polyaspartate-PEG.
Figure 3:
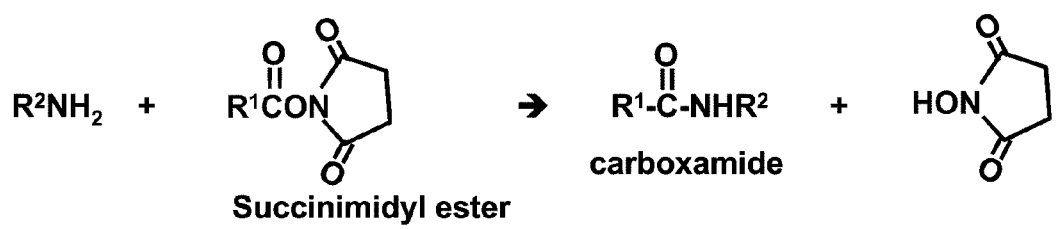
Figure 3:
Figure 4:
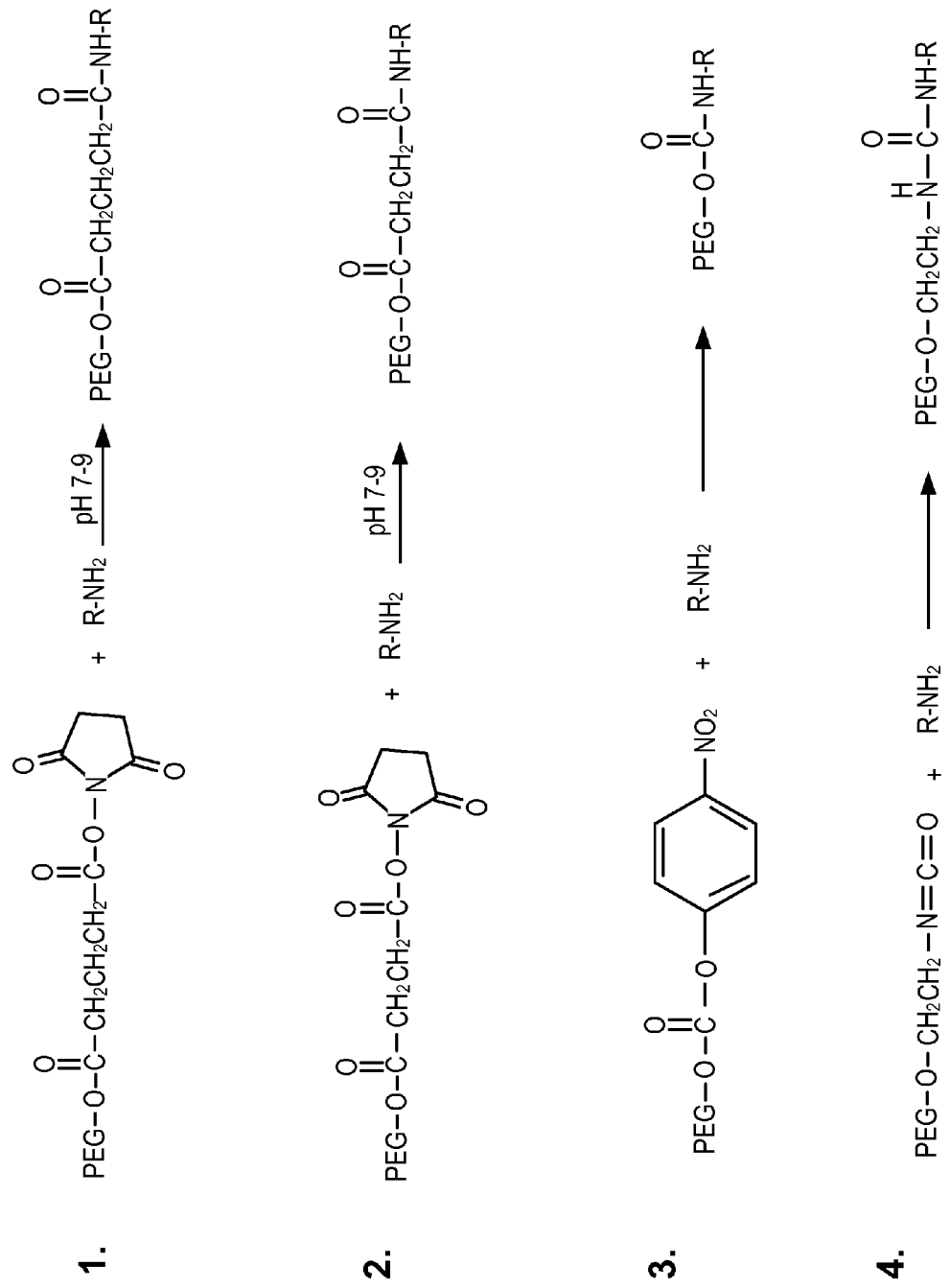
FIG. 4 depicts some of the chemical reactions that may be used to add PEG protective groups, analogs or derivatives thereof, to amino group containing polymeric backbone.
Figure 5:
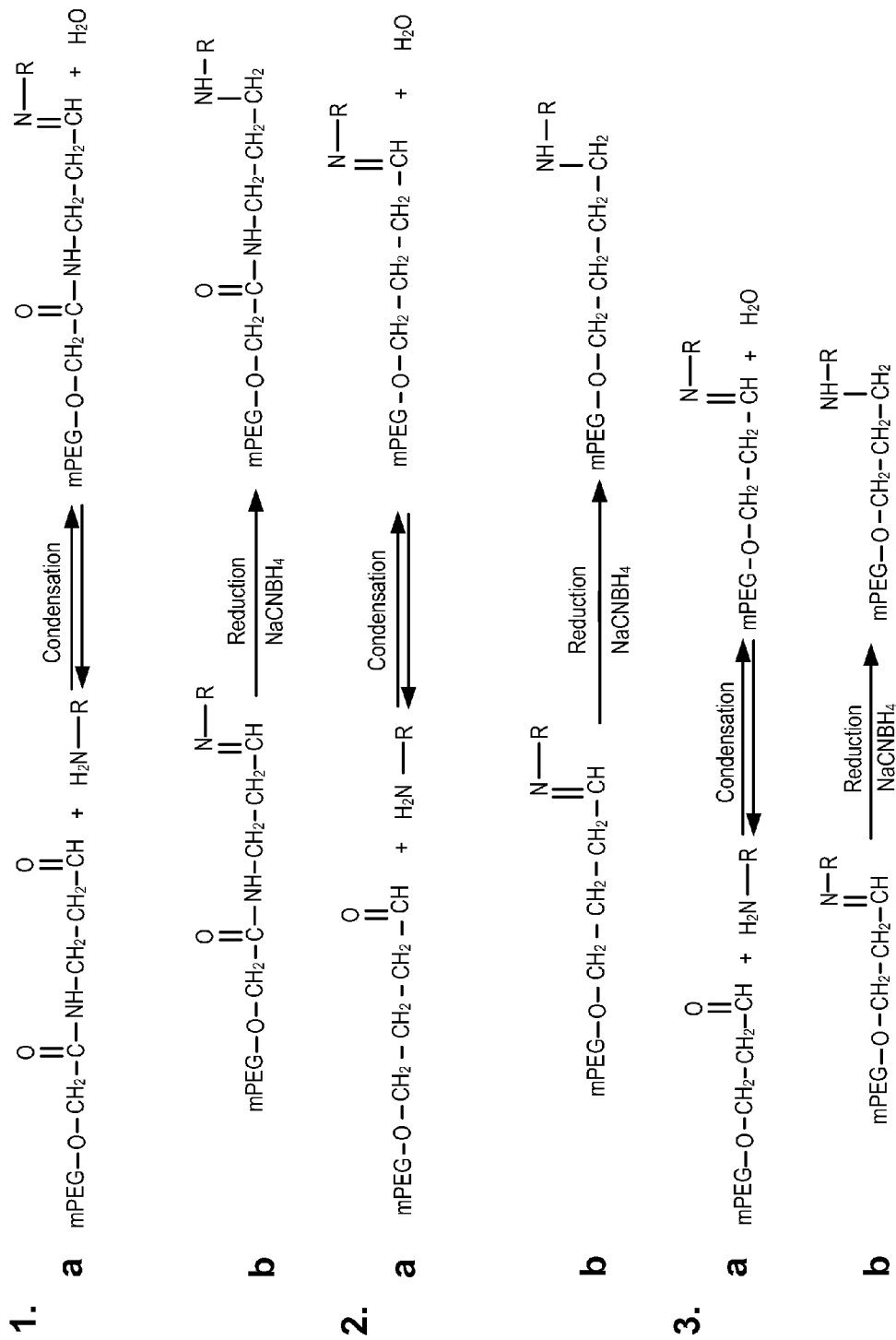
FIG. 5 depicts some of the chemical reactions that may be used to add aldehyde PEG derivatives to amino group containing polymeric backbone. These are two step condensation-reduction reactions (a & b).
Figure 6:
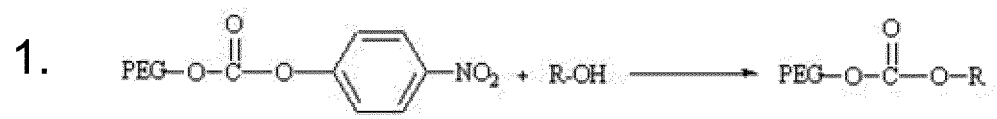
FIG. 6 depicts some of the chemical reactions that may be used to add PEG protective groups, analogs or derivatives thereof, to hydroxyl containing polymeric backbone.
Figure 6:
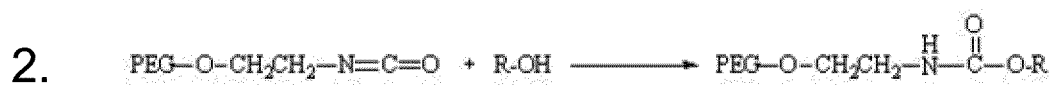
Figure 6:
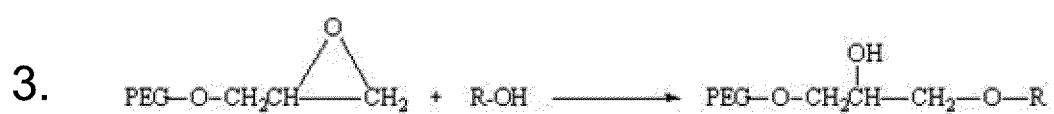
Figure 7:
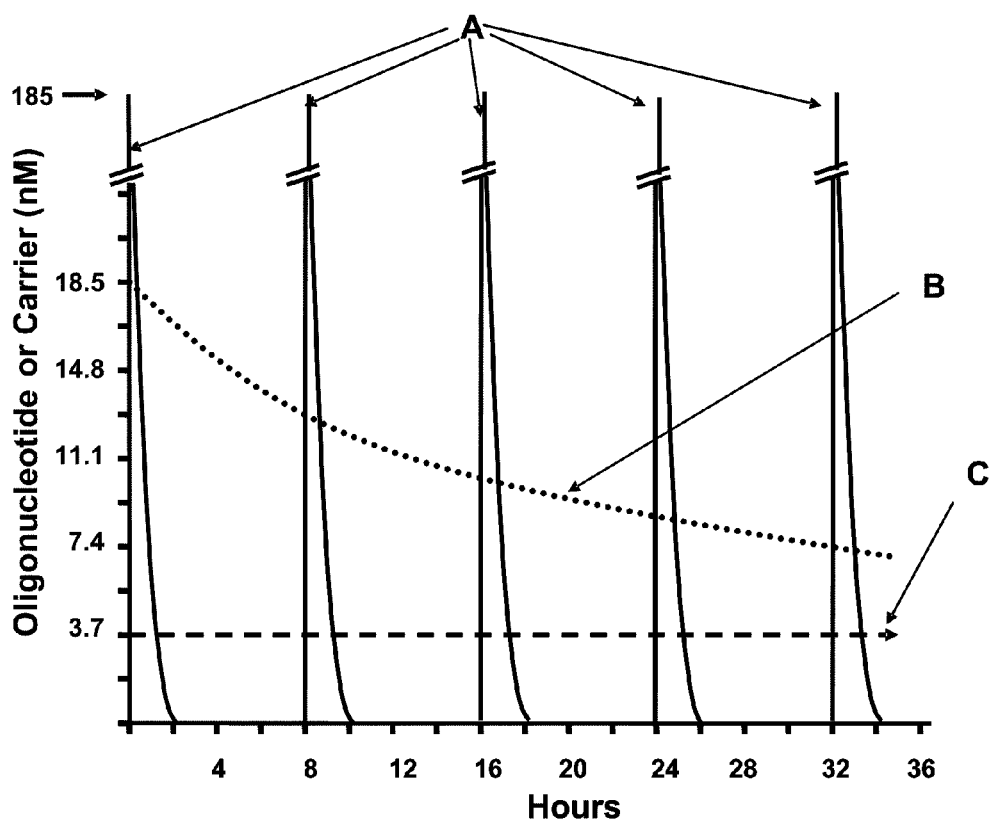
FIG. 7 is the hypothetical free hydrophobic load molecule (peptide, proteins or hydrophobic drugs) in the blood with a natural half-life of 20 minutes. There is significant fluctuation in the concentration of hydrophobic load molecule without the carrier. With the carrier, the hydrophobic load molecule will be maintained at therapeutic concentration. The nM concentration of carrier decreases with a half-life of 20 hrs. A) Hydrophobic load molecule level resulting from injection 5 mg/kg, 3 times a day without the carrier of the instant invention, this load molecule has a blood half-life of 20 minutes; B) Carrier along with load molecule has a half-life of 20 hours; C) therapeutic level of free load molecule maintained by the carrier.
Figure 8:
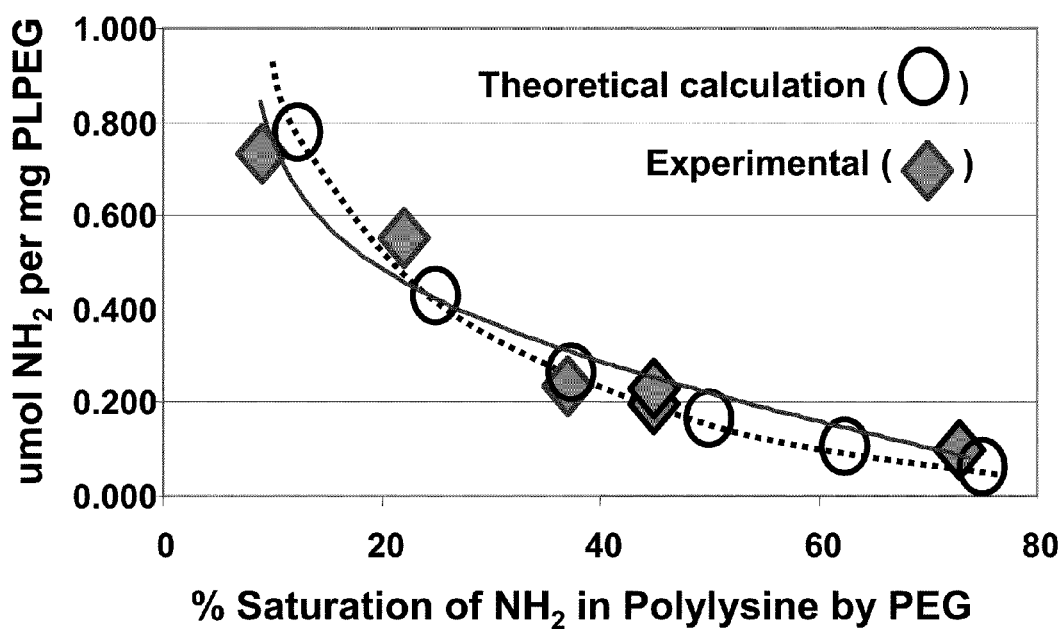
FIG. 8 is a graph showing the theoretical and actual relationship between the amount of amino-group/mg of PLPEG (polylysine-polyethyleneglycol copolymer) and amino-group saturation of polylysine. This is very useful as secondary confirmation of the composition of PLPEG. This PEGylation process is quite reproducible and adjustable during synthesis by continuing the reaction until the desired % PEGylation is achieved using TNBS amino group assay as a feedback guide during the reaction. The yield is about 50-80% (5-8 gr) of the starting materials. The theoretical prediction was calculated using the following equation: $X = [100 \times (C-Y)]/5YC+C]$; where X is the % saturation; Y is the mmol $NH_2$ per gram of PLPEG as determined by TNBS; C is the mmol of $NH_2$ per gram of PL (polylysine) as determined by TNBS. The 5 in the term 5YC in the equation represent the size of PEG used which in this case is 5 kDa, thus 5YC. If 10 kDa PEG is used, this will be 10YC. This is useful because once PLPEG product is formed, the percent saturation of the amino group of polylysine can be further confirmed by a single TNBS assay of the final product to determine Y from which X can be calculated.

Attaching Hydrophobic Moiety to Amino-Groups of Polymeric Backbone:

The present invention relates to a polymeric backbone further comprising a protective chains and hydrophobic moiety. Once the polymeric backbone contains protective chains, the hydrophobic moiety can be attached by activating carboxyl groups in hydrophobic molecule (such as fatty acids) to react with the remaining amino groups of polymeric backbone (see FIG. 3). Another object of the present invention is to provide a method of attaching hydrophobic moiety to the polymeric backbone with amino groups along its length. As an example that is not intended to limit the scope of this invention, the modifications can also be done by amide bond formation with fatty acid anhydride. Another method is to activate the carboxyl containing hydrophobic molecule using a carbodiimide containing reagent such a 1-ethyl-3-(3-dimethylaminopropyl)-carbodiimide or dicyclohexylcarbodiimide. A carbodiimide reagent contains a functional group consisting of the formula $N=C=N$. During the process of coupling reaction, the activated carboxyl group (O-acylisourea-intermediate) can optionally be stabilized by forming N-hydroxysuccinimide ester using N-hydroxysuccinimide. This relatively stable intermediate can react with the amino group of the polymeric backbone to form amino-acyl bond or amide bond. Alternatively, hydrophobic moieties can be introduced to amino groups containing polymeric backbone using fatty acyl halide. Synthesis of acyl halides can be done by reaction of the carboxylic acid moiety with dichlorosulfoxide ($SOCl_2$) or other reagent known to those skilled in the art. The resulting acyl halides are reactive to amino functional groups present in the polymeric backbone. The reaction will result in amide bond formation attaching the hydrophobic moieties or molecules to the polymeric backbone.

Attaching Hydrophobic Moiety to Carboxyl-Groups of Polymeric Backbone:

The present invention relates to a polymeric backbone with repeating carboxyl groups derivatized to contain protective chains and hydrophobic moieties. Once the polymeric backbone contains protective chains (see above), the hydrophobic moiety can be attached to the remaining carboxyl groups of the polymeric backbone by activating the carboxyl groups to react with amino containing hydrophobic molecules such as alkyl amine containing 6 to 36 carbon units or derivatives thereof. Alternatively, the activated polymeric backbone can be reacted with di-alkyl hydrophobic molecule such as phosphatidyl amine or phosphatidyl ethanolamine. Another object of the present invention is to provide a method of attaching hydrophobic moiety to the polymeric backbone with carboxyl groups along its length. As an example that is not intended to limit the scope of this invention, the modifications can be done by amide bond formation with hydrophobic molecule. The carboxyl containing polymeric backbone can be attached to the amino group of the hydrophobic moiety using a carbodiimide containing reagent such a 1-ethyl-3-(3-dimethylaminopropyl)-carbodiimide or dicyclohexylcarbodiimide. A carbodiimide reagent contains a functional group consisting of the formula N=C=N. During the process of coupling reaction, the activated carboxyl group (O-acylisourea-intermediate) can optionally be stabilized by forming N-hydroxysuccinimide ester using N-hydroxysuccinimide. This relatively stable intermediate can react with the amino group of the hydrophobic molecule to form amino-acyl bond or amide bond.

Attaching Hydrophobic Moieties to Hydroxyl-Groups of Polymeric Backbone:

The present invention relates to a polymeric backbone further comprising a protective chains and hydrophobic moiety. Once the polymeric backbone contains protective chains (see above), the hydrophobic moieties can be attached by first modifying the remaining hydroxyl groups of the polymeric backbone into a carboxyl containing group such as but not limited to reaction with succinic-anhydride or other anhydride containing molecules. Once the hydroxyl groups have been converted to carboxyl groups, the carboxyl groups can be activated to react with hydrophobic molecules containing amino groups such as alkyl amine containing 6 to 36 carbon units or derivatives thereof. Alternatively, the activated polymeric backbone can be reacted with di-alkyl hydrophobic molecule such as phosphatidyl amine or phosphatidyl ethanolamine. Another object of the present invention is to provide a method of attaching hydrophobic moiety to the polymeric backbone with hydroxyl groups along its length. As an example that is not intended to limit the scope of this invention, the modifications can be done by ester bond formation with cyclic anhydride molecule followed by amide bond formation with amino containing hydrophobic molecule. After modification of hydroxyl groups to carboxyl groups, the new carboxyl group polymeric backbone can be attached to the amino group of the hydrophobic moiety using a carbodiimide containing reagent such a 1-ethyl-3-(3-dimethylaminopropyl)-carbodiimide or dicyclohexylcarbodiimide. A carbodiimide reagent contains a functional group consisting of the formula N=C=N. During the process of coupling reaction, the activated carboxyl group (O-acylisourea-intermediate) can optionally be stabilized by forming N-hydroxysuccinimide ester using N-hydroxysuccinimide. This relatively stable intermediate can react with the amino group of the hydrophobic moiety to form amino-acyl bond or amide bond.

Attaching Protective Group-Containing Hydrophobic Molecules to Polymeric Backbone:

The present invention relates to a polymeric backbone further comprising a protective chains pendant to the backbone; hydrophobic moiety pendant to the backbone, and second protective chains covalently linked to the hydrophobic moieties. A two ended hydrophobic molecule such as thapsic acid can easily be attached to the amino group containing protective chains. Limiting activation can be performed on thapsic acid such that most of the molecules are singly activated. This can be done by using one half molar equivalent (compared to thapsic acid) of a carbodiimide containing reagent such a 1-ethyl-3-(3-dimethylaminopropyl)-carbodiimide or dicyclohexylcarbodiimide compared to thapsic acid. A carbodiimide reagent contains a functional group consisting of the formula N=C=N. During the process of coupling reaction, the activated carboxyl group (O-acylisourea-intermediate) can optionally be stabilized by forming N-hydroxysuccinimide ester using N-hydroxysuccinimide (one molar equivalent to thapsic acid). Once activated and stabilized, the thapsic acid will have mostly singly activated end which can then be reacted to amino containing protective chains. If the protective chains or molecule does not have an amino group, the amino group can be introduced to this molecule very easily and the chemistry is well known to those skilled in the art. More details in the synthesis of various embodiment of the composition can also be seen in U.S. patent application Ser. No. 11/613,183 which hereby incorporated by reference and to which this application claims priority.

The type of chemical link to use in attaching the hydrophobic moiety and protective groups will depend on the desired biological half-life of the complex and the therapeutic agent associated with the complex. If longer half-life is desired amide bonds will be preferred, while ester bonds will be used for carrier that need shorter half-lives or stabilities in biological fluid or tissue. Mixtures of both chemical bonds can be used to achieve the desired stability for a specific therapeutic agent to be delivered. The S—S bond may be used to achieve a desired property of the carrier that would be beneficial for its intended therapeutic and diagnostic purpose.

These embodiments of the present invention, other embodiments, and their features and characteristics, will be apparent from the description, drawings and claims that follow.

EXEMPLIFICATION

Synthetic Method Overview

Hydrophobic core carriers of the present invention include a central polymeric backbone, a hydrophobic moiety, a protecting group, and, optionally hydrophobic moiety and/or a targeting group. Each group is linked together covalently and the hydrophobic moiety group is capable of forming reversible binding (hydrophobic interaction) with hydrophobic load molecule (therapeutic or diagnostic agent) such as hydrophobic peptides/proteins, hydrophobic drugs and derivatives thereof. The reversible linkage between the carrier and a load molecule includes hydrophobic interactions between the hydrophobic load molecule and the hydrophobic moiety of the carrier.

The synthesis of hydrophobic-core carrier from a polymeric backbone containing amino, carboxyl, hydroxyl groups, or thiol groups generally involves three synthetic stages: 1) covalent modification of a back bone carrier with protective chains; 2) modification of the product from step 1 with a hydrophobic moiety; and 3) incubating the product from step 2 with a load molecule, for example with leptin, to achieve formation of a hydrophobic core carrier-leptin complex without vesicle formation.

Example 1

Figure 9:
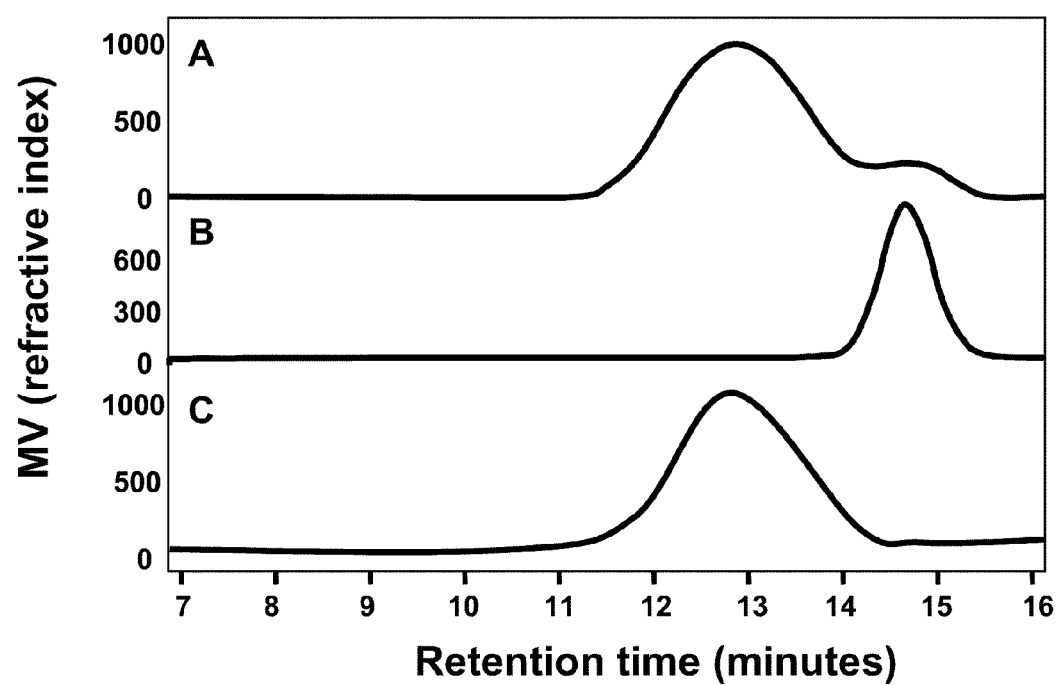
FIG. 9. These are Gel Filtration Chromatograms of the products of the reaction before and after clean up through 100 kDa MWCO membrane (Amersham Biosciences, Needham, Mass.) showing that all unreacted PEG had been removed. The column used was Ultrahydrogel linear (0.78×30 cm, Waters) eluted at flow rate of 0.6 ml/min PBS with 15% Acetonitrile. The materials were detected using refractive index detector. Panel A is 20PLPEG555 (20 kDa polylysine where 55% of the amino groups were reacted with PEG succinate of 5 kDa molecular weight) prior to clean-up from unreacted 5 kDa PEG. Panel B is 5 kDa PEG alone. Panel C is 20PLPEG555 after clean up.
Figure 10:
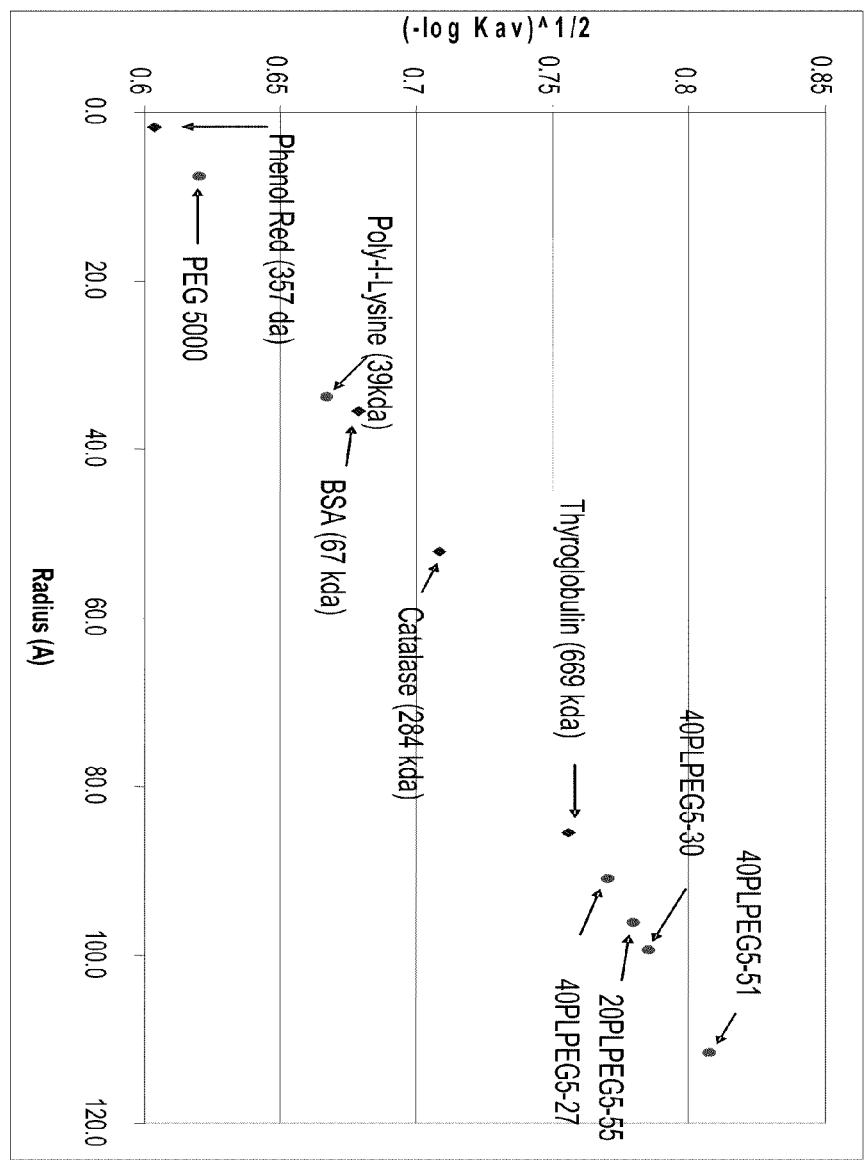
FIG. 10. These are the Stoke's radii of various carriers along with proteins of known stokes radii. These were analyzed on the Ultrahydrogel Linear column (0.78 cm diameter×30 cm length) using PBS with 15% Acetonitrile at a flow rate of 0.6 ml/min as mobile phase. The 20PL-PEG555 (20 kDa polylysine where 55% of the amino groups were reacted with PEG succinate of 5 kDa molecular weight), 40PL-PEG530 (40 kDa polylysine where 30% of the amino groups were reacted with PEG succinate of 5 kDa molecular weight), 40PL-PEG551 (40 kDa polylysine where 51% of the amino groups were reacted with PEG succinate of 5 kDa molecular weight), and 40PL-PEG527 (40 kDa polylysine where 27% of the amino groups were reacted with PEG succinate of 5 kDa molecular weight) are larger than the glomerular filtration cut off that is above 4 nm (40 Angstrom) in diameter (or 20 Angstrom in radius). Proteins with known stokes radii were used as reference including Thyroglobulin (669 kDa; 85.5 Angstroms stokes radius), Catalase (248 kDa; 52.2 Angstrom stokes radius), and BSA (67 kDa; 35.5 Angstroms stokes radius), Catalase (248 kDa; 52.2 Angstrom stokes radius), and BSA (67 kDa; 35.5 Angstrom stokes radius).
Figure 11:
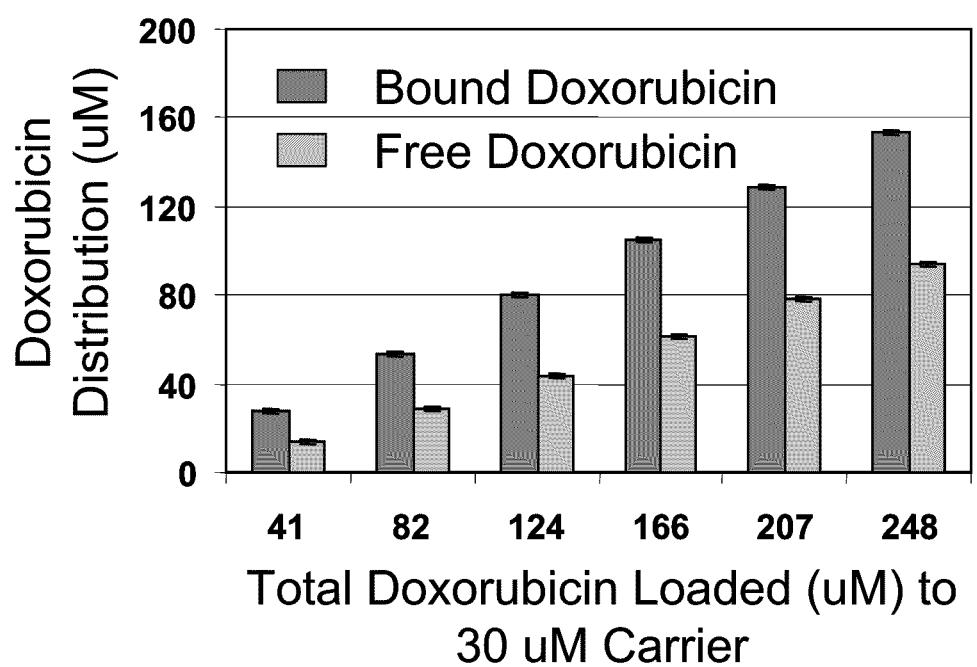
FIG. 11. Binding of Doxorubicin-HCl to a carrier comprising 20 kDa polylysine backbone, 55% of the amino residues were covalently linked to 5 kDa MPEGsuccinate, and the remainder saturated with stearic acid. Ten mg/ml (30 uM) of Carrier is loaded with various concentration of doxorubicin. This specific carrier binds doxorubicin but did not bind with strong affinity. When Scatchard plot is used and has apparent Kd of 315 uM. This is not considered strong binding since to be considered strong for the purpose of the present invention Kd has to be less than 100 uM. The relative hydrophilicity of doxorubicin is evident from its retention time on reverse phase HPLC column (Table 3, below) compared to other load molecules tested.
Figure 12:
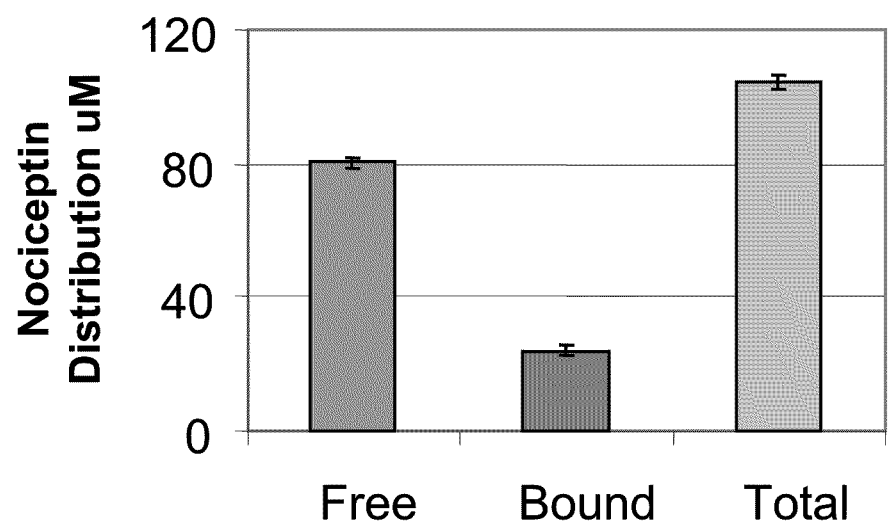
FIG. 12. Binding of Nociceptin to a carrier comprising 20 kDa polylysine backbone, 55% of the amino residues were covalently linked to 5 kDa MPEGsuccinate, and the remainder saturated with stearic acid. Ten mg/ml (30 uM) of Carrier is loaded with 0.2 mg/ml (111 uM) Nociceptin. This specific carrier binds Nociceptin but did not bind with strong affinity. Very little binding is observed as consistent with its hydrophilicity and the early retention time (1.43 minutes; see table 3 below) on HPLC compared with the retention time of GLP-1 (2.5 minutes; see table 3 below) in identical reversed phase HPLC column (SynergiMaxRP 4×20 mm; Phenomenex). The column was eluted at a flow rate of 1.5 ml/min using a gradient of solvent A to B (25-50% B from 1-5 minutes) where A is water with 0.1% Trifluoroacetic acid (TFA)/5% Acetonitrile and solvent B is Acetonitrile with 0.1% TFA.
Figure 13:
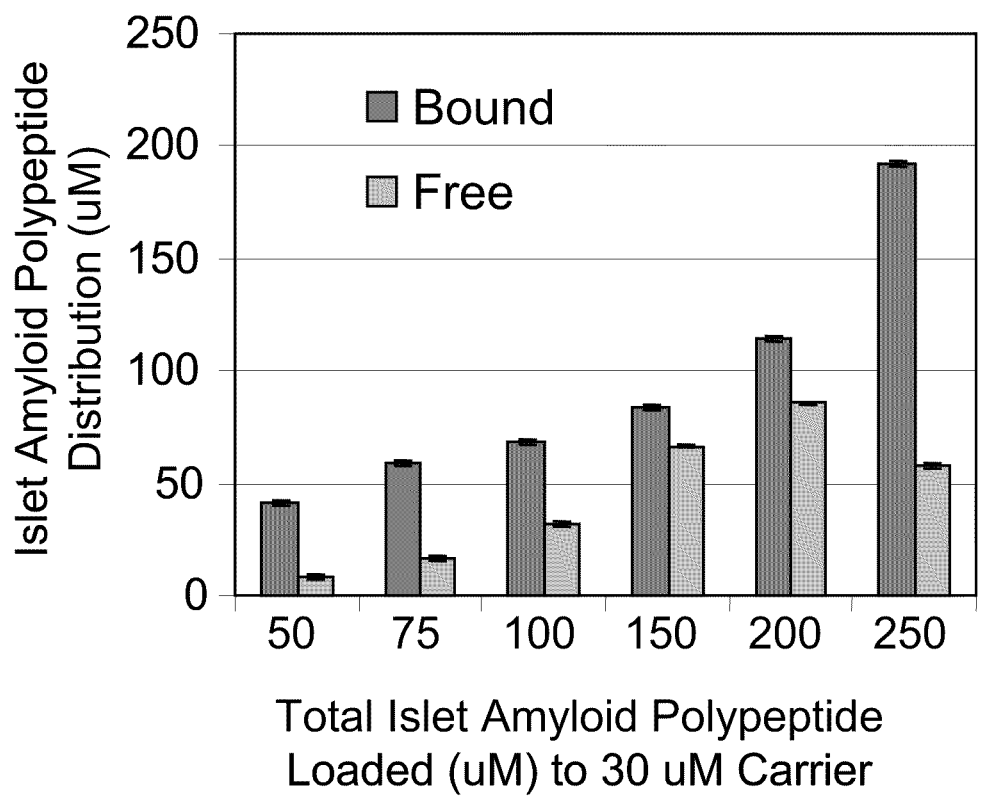
FIG. 13. Binding of Islet Amyloid Polypeptide or IAPP to a carrier comprising 20 kDa polylysine backbone, 55% of the amino residues were covalently linked to 5 kDa MPEGsuccinate, and the remainder saturated with stearic acid. Ten mg/ml (30 uM) of Carrier is loaded with various amount IAPP (for methods see example 9). This carrier binds IAPP with strong affinity and will be useful in prolonging the blood circulation half-life of IAPP or its derivative when administered with the carrier. When analyzed by Scatchard plot, the binding has Kd of 900 nM. The relative hydrophobicity of IAPP based on reverse phase HPLC retention time is shown in Table 3 below.
Figure 14:
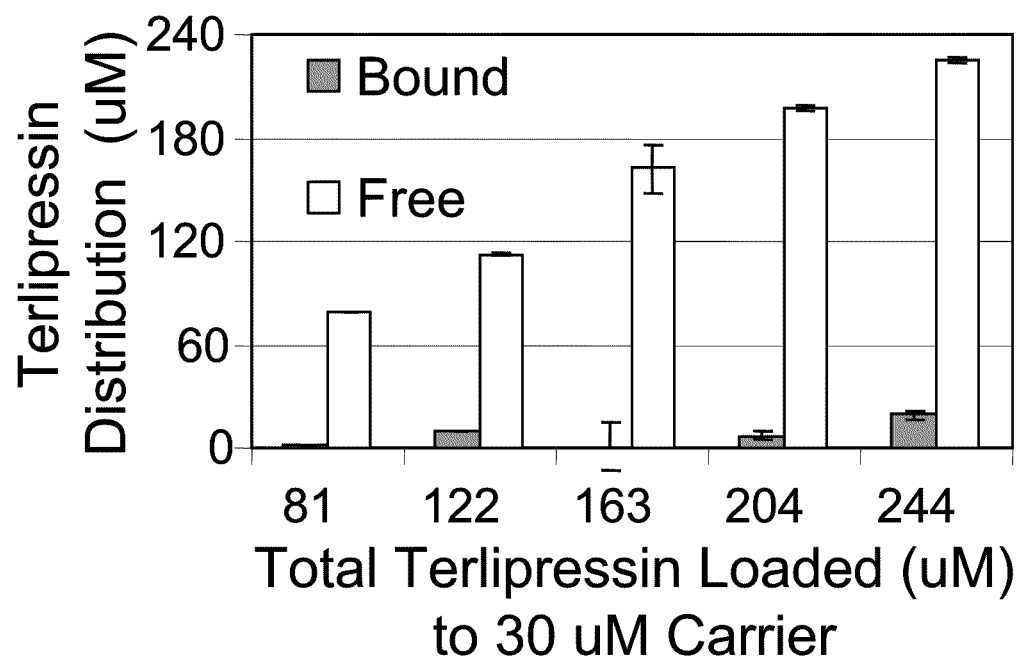
FIG. 14. Binding of Terlipressin to a carrier comprising 20 kDa polylysine backbone, 55% of the amino residues were covalently linked to 5 kDa MPEGsuccinate, and the remainder saturated with stearic acid. Ten mg/ml (30 uM) of Carrier is loaded with various amount Terlipressin (for methods see example 9). This carrier does not bind Terlipressin with strong affinity. The relative hydrophobicity of terlipressin based on reverse phase HPLC retention time is shown in Table 3 below.
Figure 15:
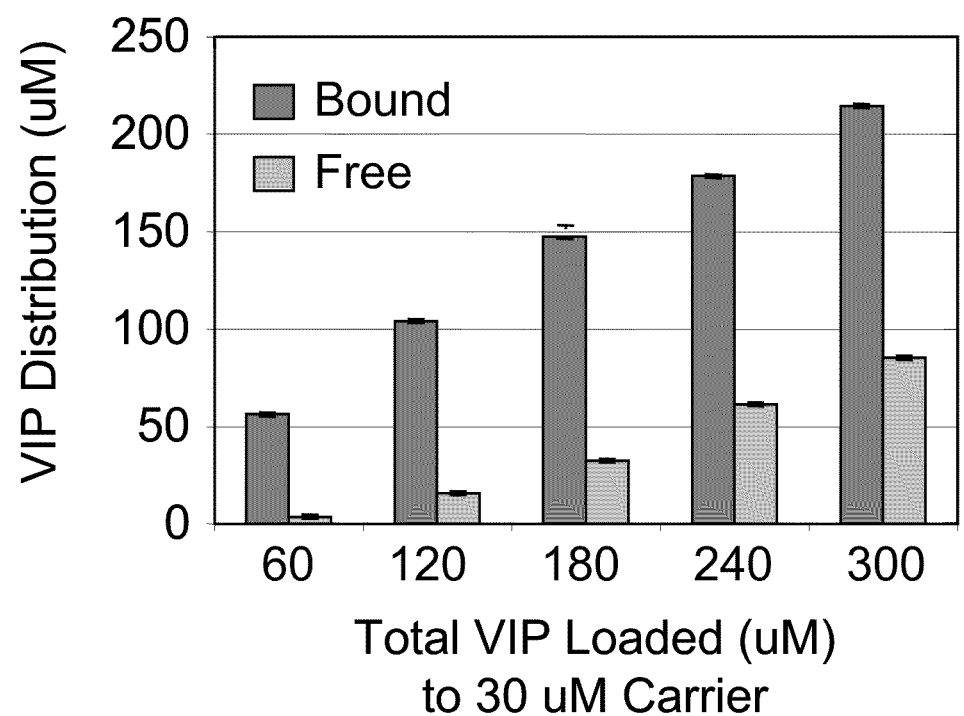
FIG. 15. Binding of Vasoactive Intestinal Peptide (VIP) to a carrier comprising 20 kDa polylysine backbone, 55% of the amino residues were covalently linked to 5 kDa MPEGsuccinate, and the remainder saturated with stearic acid. Ten mg/ml (30 uM) of Carrier is loaded with various amount VIP (for methods see example 9). This carrier binds VIP with strong affinity and will be useful in prolonging the blood circulation half-life of VIP when administered with the carrier. The relative hydrophobicity of VIP based on reverse phase HPLC retention time is not greater than human growth hormone as shown in Table 3 below. It is surprising that growth hormone did not bind to the carrier with strong affinity while VIP which is less hydrophobic did. Further investigation indicated that at neutral pH in the presence of lipid (or perhaps carrier of the present invention), VIP assumes more hydrophobic alpha helix structure. Polypeptides such as this run under acidic HPLC conditions will not follow the general trend and must be run under neutral non-denaturing HPLC conditions to be more predictive.
Figure 16:
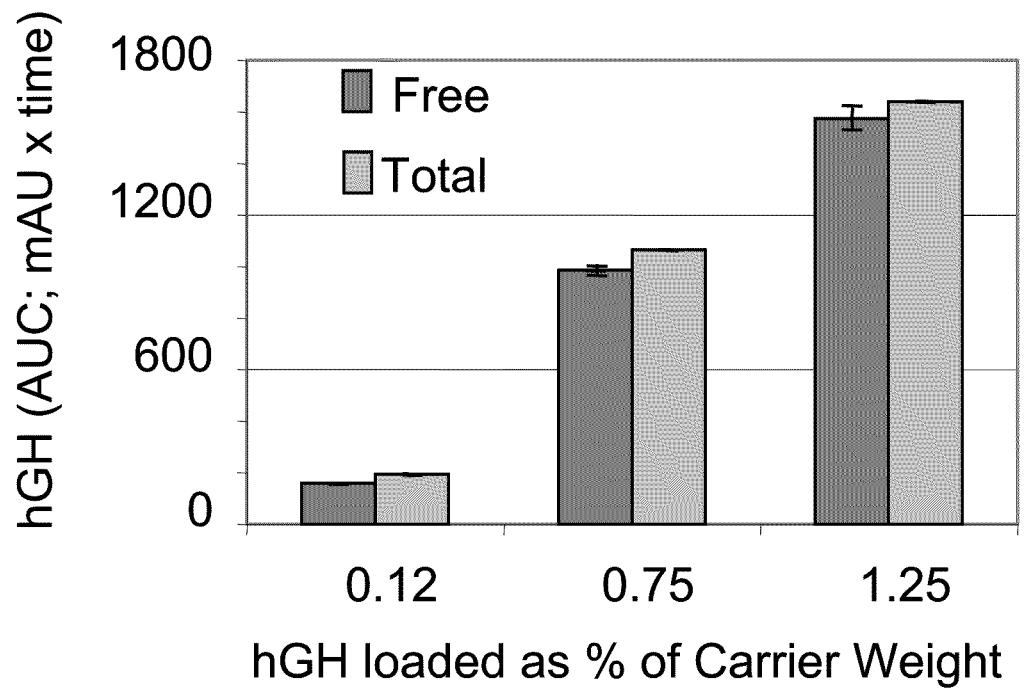
FIG. 16. Binding of recombinant human growth hormone (hGH) to a carrier comprising 20 kDa polylysine backbone, 55% of the amino residues were covalently linked to 5 kDa MPEGsuccinate, and the remainder saturated with stearic acid. Ten mg/ml (30 uM) of Carrier is loaded with various amount hGH (for methods see example 9). This carrier does not bind hGH with strong affinity.
Figure 17:
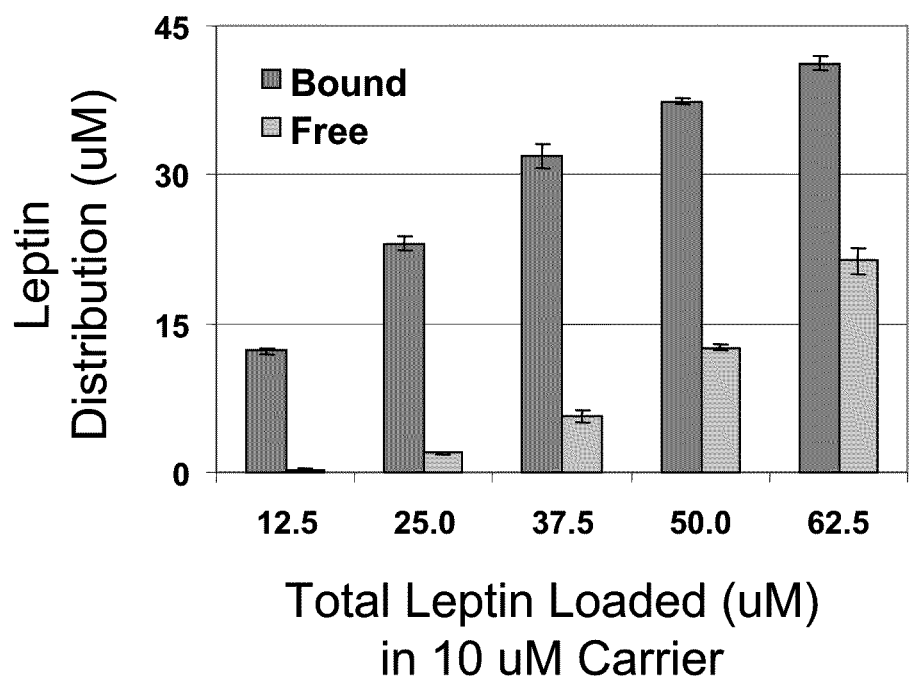
FIG. 17. Binding of Leptin to a carrier comprising 20 kDa polylysine backbone, 55% of the amino residues were covalently linked to 5 kDa MPEGsuccinate, and the remainder saturated with stearic acid. 33 mg/ml (10 uM) of Carrier is loaded with various amount Leptin (for methods see example 9). The carrier binds Leptin with strong affinity and when analyzed by Scatchard plot, the binding has Kd of 700 nM. This carrier will be useful in prolonging the blood circulation half-life of Leptin when administered with the carrier.

Synthesis of MPEG-poly-L-lysine (5000; 40,000; 27%; 40PLPEG527): The reagents, MPEG-succinimidyl-succinate and polylysine, are commercially available and their syntheses are well known in the art. Poly-L-lysine (200 mg; Polylysine Hydrobromide; Sigma chemical Co.; DPvis: 264; MWvis: 55,200; DPmalls: 190; MWmalls: 39,800; 0.7 mmoles amino groups by TNBS assay by Sparado et al. Anal Biochem 96:317, 1979) was dissolved in 200 ml of 0.1 M carbonate buffer pH 8.35 and 1150 mg of MPEG-succinimidyl-succinate (pre-activated 5 kDa PEG from NOF, Tokyo, Japan) was added, vortexed followed by overnight incubation at room temperature. The next day, aliquots were taken and the amount of amino groups remaining was quantified using trinitrobenzenesulfonic acid (Sparado et al. Anal Biochem 96:317, 1979). The result indicated that 73% of amino group remains. The solution (200 ml) was washed by ultra-filtration through 100 kDa cut-off membrane (UFP-100-E-3A, GE-Amersham Biosciences Corp, Westborough, Mass.) with ten changes of water. The resulting PLPEG complex was lyophilized and weighed giving a yield of 860 mg. The resulting product has an estimated Mw of 310 kDa based on the number of amino groups that had been derivatized by MPEG. The number of free amino groups per mg of final product is 0.43 umole/mg (FIG. 9).

Example 2

Synthesis of MPEG-poly-L-lysine (5 kDa PEG; 40 kDa PL; 55% saturation of amino groups; 40PLPEG555): The reagents, MPEG-succinimidyl-succinate and polylysine, are commercially available and their syntheses are well known in the art. One gm of 40PL (Polylysine Hydrobromide; Sigma chemical Co.; DPvis: 264; MWvis: 55,200; DPmalls: 190; MWmalls: 39,800; one gram contains 3.0 mmol amino groups) was dissolved in 190 ml of 200 mM HEPES. Five grams (1 mmol) of MPEG-succinimidyl-succinate (pre-activated 5 kDa PEG from NOF, Tokyo, Japan) was added to 40PL solution and allowed to react. After 2 hrs, additional 5 g of MPEG-succinimidyl-succinate was added as above and allowed to react over the weekend. Amino group content was measured by TNBS (Sparado et al. Anal Biochem 96:317, 1979) and found to be 1.4 mmol total indicating 53% saturation of amino group. The solution (200 ml) was washed by filtration through 100 kDa cut-off membrane (UFP-100-E-5A, GE-Amersham Biosciences Corp, Westborough, Mass.) with ten changes of water. The resulting PLPEG complex was lyophilized and weighed giving a yield of 8.6 g. The resulting product has an estimated Mw of 570 kDa based on the number of amino groups that had been derivatized by MPEG. The number of free amino groups per mg of final product is 0.20 umole/mg (FIG. 9).

Example 3

Synthesis of MPEG-poly-1-lysine (5 kDa PEG; 40 kDa PL; 22% saturation of amino groups; 40PLPEG522): The reagents, MPEG-succinimidyl-succinate and polylysine, are commercially available and their syntheses are well known in the art. Poly-L-lysine (200 mg; Polylysine Hydrobromide; Sigma chemical Co.; DPvis: 264; MWvis: 55,200; DPmalls: 190; MWmalls: 39,800; 0.7 mmoles amino group by TNBS assay Sparado et al. Anal Biochem 96:317, 1979) was dissolved in 10 ml of 0.2 M HEPES buffer pH 7.35 and 500 mg of MPEG-succinimidyl-succinate (pre-activated 5 kDa PEG from NOF, Tokyo, Japan) was added, vortexed, repeated (another 500 mg) and incubated overnight at room temperature. The next day, aliquots were taken and the amount of amino groups remaining was quantified using trinitrobenzene-sulfonic acid (Sparado et al. Anal Biochem 96:317, 1979). The result indicated that 22% of amino groups had been conjugated to MPEG. The solution was washed by ultra-filtration through 100 kDa cut-off membrane (UFP-100-E-3A, GE-Amersham Biosciences Corp, Westborough, Mass.) with ten changes of water. The resulting PLPEG complex was lyophilized and weighed giving a yield of 820 mg. The resulting product has an estimated Mw of 260 kDa based on the number of amino groups that had been derivatized by MPEG. The number of free amino groups per mg of final product is 0.40 umole/mg (FIG. 9).

Example 4

Synthesis of 20PLPEG555 DA (5 kDa MPEGcarboxyl; 20 kDa PL; 55% saturation of amino groups; 20PLPEG555DA).

The MPEG used in this synthesis is carboxyl MPEG without ester bond resulting in direct amide (DA) connection to polymeric backbone without ester bond which is different than succinate ester MPEG above where the linkage between the MPEG and succinate is ester bond. One gm of 20PL (P7890 Sigma lot#065K5101; one gram contains 2.4 mmol amino groups) was dissolved in 50 ml of 200 mM HEPES. Five grams (1 mmol) of MPEGCarboxyl (pre-activated but lost some activation; NOF, Tokyo, Japan) in 15 ml of 10 mM MES pH=4.7 was re-activated by adding 250 mg of NHSS (mw=217.14; 1.15 mmol, followed by 500 mg EDC (mw=191.71; 2.6 mmol). Activation is allowed to proceed for 20 minutes. The activated MPEGCarboxyl was added to 20PL solution and allowed to react. After 2 hrs, additional 5 grams of MPEGCarboxyl was activated and added as above and allowed to react over the weekend. Amino group was measured by TNBS (Sparado et al. Anal Biochem 96:317, 1979) and found to be 1.05 mmol total indicating 56% saturation of amino group. This was confirmed by Size Exclusion chromatography using TosohG4000WXL with Retention time of 12.35 min (17 nm). The solution was washed by ultra-filtration through 100 kDa cut-off membrane (UFP-100-E-5A, GE-Amersham Biosciences Corp, Westborough, Mass.) and lyophilized (9.9 g). One gm was saturated with FITC for determination of carrier Cmax (maximum concentration in blood) and Tmax (Time for maximum concentration in blood) in animals and washed with ethanol, water and lyophilized (960 mg). The remaining 8.9 g of 20PLPEG555DA was divided into 2 (in 53 ml DCM each) and one was saturated with activated C22 (2.5 mmol in 30 ml in 2:1 DMF:DCM) and the other was saturated with C18 (2.5 mmol in 30 ml in 2:1 DMF:DCM) below.

Example 5

Synthesis of 20PLPEG555DAC18 and 20PLPEG555DAC22. The remaining 8.9 g of 20PLPEG555DA was divided into 2 (in 53 ml DCM each) and one was saturated with activated behenic acid and the other is saturated with activated stearic acid.

Behenic acid or C22 (0.851 gm or 2.5 mmol in 30 ml in 2:1 DMF:DCM) was activated by adding 290 mg NHS (Mw=115; 2.5 mmol) and 1 ml DCC (Mw=206; 1 ml=1.3 g=6.3 mmol) and incubating for an hour. The urea precipitate was removed by centrifugation and the supernatant was added to the 20PLPEG555DA solution along with 200 ul TEA and allowed to react. This was repeated twice and allowed to react overnight. The product was rotary evaporated at 37° C., dissolved in 80% ethanol and precipitate was removed by centrifugation. The supernatant (200 ml) was washed with 3 liter of 80% ethanol followed by 1 liter of water. This was filter-sterilized using 200 nm filter and lyophilized giving 2.9 g. Note that insoluble compositions will not go through this filter-sterilization: compositions with PEG/Fatty acid weight ratio of less than 14 (see table 2) and those that form vesicles. The diameter of the composition is 19.8 nm with retention time of 12 minutes in gel permeation chromatography using G4000PWXL column (0.78×30 cm; TSK Gel; Tosoh Biosep; Montgomeryville, Pa.) eluted with PBS containing 15% acetonitrile at flow rate of 0.6 ml/min. Amino group content is 18 nmol/mg (very small). The composition is water soluble at 100 mg/ml forming a yellowish true solution without cloudiness. The composition does not form vesicles upon addition of cholesterol.

Stearic acid or C18 (0.7 gm or 2.5 mmol in 30 ml in 2:1 DMF:DCM) was activated by adding 290 mg NHS (Mw=115; 2.5 mmol) and 1 ml DCC (Mw=206; 1 ml=1.3 g=6.3 mmol) and incubating for an hour. The urea precipitate was removed by centrifugation and the supernatant was added to the 20PLPEG555DA solution along with 200 ul TEA and allowed to react. This was repeated twice and allowed to react overnight. The product was rotary evaporated at 37 C, dissolved in 80% ethanol, precipitate was removed by centrifugation, and supernatant was washed with 2 liter of 80% ethanol after followed by water. This was filter sterilized using 200 nm filter and lyophilized giving 3.35 g. Note that insoluble compositions will not go through this filter sterilization especially those that form vesicles. Diameter is 19.4 nm with retention time of 12.05 minutes. Amino group content is 6 nmol/mg (very small). The composition is water soluble at 100 mg/ml forming a yellowish true solution without cloudiness. The composition does not form vesicles upon addition of cholesterol.

Example 6

Reproducibility of the synthesis of 20PLPEG555C18: The carrier 20PLPEG555C18 which is made up of 20 kDa polylysine (from Sigma Chemical Co. with degree of polydispersity of 1.2), wherein 55 percent of the TNBS reactive amino groups was reacted with 5 kDa MPEG-ester-succinate and the remaining 44-45% the TNBS reactive amino groups was conjugated with stearic acids, was made. To make this, one gm of 20PL (P7890 Sigma lot#065K5101; 1 gm has 2.4 mmol NH2) was dissolved in 50 ml of 200 mM HEPES. Five grams of MPEG-succinate (1 mmol) in 15 ml of 10 mM MES pH=4.7 was activated by adding 250 mg of NHSS (mw=217.14; 1.15 mmol, followed by 500 mg EDC (mw=191.71; 2.6 mmol). Activation is allowed to proceed for 20 minutes. The activated MPEG-succinate was added to 20PL solution and allowed to react. After 2 hrs, additional five grams of MPEG-succinate was activated and added as above and allowed to react over the weekend. Amino group was measured and found to be 1.017 mmol indicating 57% saturation of amino group. This was confirmed by Size Exclusion chromatography using TosohG4000WXL (flow rate of 0.6 ml/min; in PBS with 15% acetonitrile) with retention time of 12.9 min (14 nm) also showing 90% incorporation of total PEG added. The reaction mixture containing the 20PLPEG555 was lyophilized and dissolved in 50 ml DCM, precipitates were removed by centrifugation, precipitates were washed with DCM, and the pooled supernatant (total 200 ml) was saturated with activated C18 after addition of 400 ul TEA. To do this, stearic acid (C18; 0.7 gm or 2.5 mmol in 30 ml in 1:2 DMF:DCM) was activated by adding 290 mg NHS (Mw=115; 2.5 mmol) and 0.5 ml DCC (Mw=206; 0.5 ml=0.65 g=3.2 mmol) and incubating for an hour. The urea precipitate was removed by filtration and the activated fatty acid was added to the 20PLPEG555 solution and allowed to react. This was repeated twice and allowed to react overnight, followed by rotary evaporation of the reaction mixture, dissolution in 50% ethanol water and removal of the precipitate and top fatty layer by centrifugation. The precipitate was washed twice with 50% ethanol and all supernatants were pooled together and made up to 80% ethanol to clarify the solution before ultra-filtration. The pooled supernatant was concentrated to 200 ml using ultra-filtration apparatus (100,000 MWCO Ultra-filtration cartridge; UFP-100-E-5A, GE-Amersham), washed with 10 volumes of 80% ethanol followed by 10 volumes of water in the same ultra-filtration apparatus, concentrated 150 ml and collected. The remaining material in cartridge was washed with 2×50 ml water to and pooled with the sample. Sample (20PLPEG555C18) was filtered sterilized using 0.2 um filter (polysulfone membrane; Nalgene) and lyophilized (total 8.9 grams). It should be noted that the insoluble materials will not go through this filter as well as materials greater than 0.2 um. The molecular diameter of the carrier was determined by Exclusion chromatography using TosohG4000WXL (flow rate of 0.6 ml/min; in PBS with 15% acetonitrile) and found to have 12 minute retention time corresponding to 19 nm using globular protein standards. One mg/ml of 20PLPEG555C18 was analyzed by TNBS and found contain 6+/−5 uM NH2 or 6 nmol/mg indicating greater than 90% saturation.

The above synthesis was repeated two more times to determine reproducibility. The resulting carrier is water soluble and has diameter of 19 nm and retains load molecule by affinity. Acid digestion and amino acid analysis indicated that the overall lysine content of the composition is 4.8 to 5% by weight. The acid digestion used is similar to the analysis done in with protein and is know to those skilled in the art. The following table shows the results of the triplicate synthesis of the carrier showing the reproducibility of the synthesis.

TABLE 1

|  | 20PLPEG555C18 Lot # | | |
| --- | --- | --- | --- |
|  | A | B | C |
| Polylysine degree of polymerization (Polydispersity Mn/Mw) | 115 (1.2) | 115 (1.2) | 115 (1.2) |
| % PEG Sat | 54% | 54% | 55% |
| Retention Time Before Fatty acid Addition (min) | 12.9 | 12.9 | 12.9 |
| Size Diameter of PLPEG | 14 nm | 14 nm | 14 nm |
| Carrier Retention Time After Fatty acid Addition (min) | 12.16 | 12.22 | 12.03 |
| Carrier Diameter | 19 nm | 18 nm | 19 nm |
| Yield (based on starting PEG plus Polylysine weight as 100%) | 79% | 81% | 81% |
| Amount | 8.9 g | 9.2 g | 4.5 g |
| NH2 left in Carrier (started at 3 umol/mg PL; % +/− STD) | 6 nmol/mg (4 +/− 2%) | 8 nmol/mg (5.2 +/− 2%) | 10 nmol/mg (6.6 +/− 2%) |
| GLP1 loading test (% loaded +/− STD when GLP1 at 2% of carrier weight was loaded in 10 mg/ml Carrier) | 95.8 +/− 0.05 | 96.1 +/− 0.43 | 95.9 +/− 0.09 |
| Lysine content by weight after complete acid digestion | 4.96% | 4.87% | 4.82% |

Example 7

The following experiments were performed to determine the solubility properties of various compositions of Polylysine/Fatty acids/MPEG conjugates. The transition to become water soluble at 50 mg/ml started when the MPEG:fatty acid weight ratio is somewhere between 12:1 and 14:1. All compositions in which the MPEG:fatty acid weight ratio is at least 14:1 are water soluble. This provides a composition that is soluble in the absence of cholesterol and non-vesicle forming even in the presence of cholesterol when mixed in aqueous solvent or partially aqueous solvent. The methods to synthesize the following compositions shown in table 2 are as in example 6. To vary the percent of MPEG in the composition the amount of MPEG in the synthesis was varied proportionately and added in small portion with amino group measurement in between until the desired amino groups saturation was achieved. With the exception of C8 and C12, the fatty acids were activated with NHS and DCC. For C8, C12 and C16, the caprylic, lauric, and palmitic anhydride reagents were used instead of activating the caprylic, lauric, and palmitic acids. For each composition the solubility was noted at 50 mg/ml and data are presented in Table 2.

TABLE 2

Shown are the solubility properties of various compositions of Polylysine/Fatty acids/MPEG conjugates

| % Amino groups in polylysine linked to MPEG (size in kDa) | % Amino groups in polylysine linked to Fatty acid (type) | MPEG:Fatty acid weight ratio | Water solubility at 50 mg/ml |
|---|---|---|---|
| 55 (5 kDa) | 44 (C8) | 43 | Soluble |
| 35 (5 kDa) | 64 (C4) | 31 | Soluble |
| 55 (5 kDa) | 44 (C16) | 24 | Soluble |
| 55 (5 kDa) | 44 (C18) | 22 | Soluble |
| 37 (5 kDa) | 62 (C8) | 20 | soluble |
| 35 (5 kDa) | 64 (C8) | 19 | Soluble |
| 55 (5 kDa) | 44 (C22) | 18 | Soluble |
| 55 (5 kDa) | 44 (C24) | 17 | Soluble |
| 37 (5 kDa) | 62 (C12) | 15 | Soluble |
| 35 (5 kDa) | 64 (C12) | 13.7 | Partially soluble |
| 26 (10 kDa) | 73 (C18) | 12.5 | Partially soluble |
| 37 (5 kDa) | 62 (C16) | 11.6 | Partially soluble |
| 37 (5 kDa) | 62 (C18) | 10.5 | Insoluble gel |
| 27 (5 kDa) | 72 (C16) | 7.3 | Insoluble gel |
| 27 (5 kDa) | 72 (C18) | 6.6 | insoluble gel |
| 27 (5 kDa) | 72 (C24) | 5.0 | Insoluble gel |
| 9 (5 kDa) | 90 (16) | 1.95 | Insoluble gel |
| 9 | 90 (C18) | 1.76 | Insoluble gel |

Example 8

Figure 18:
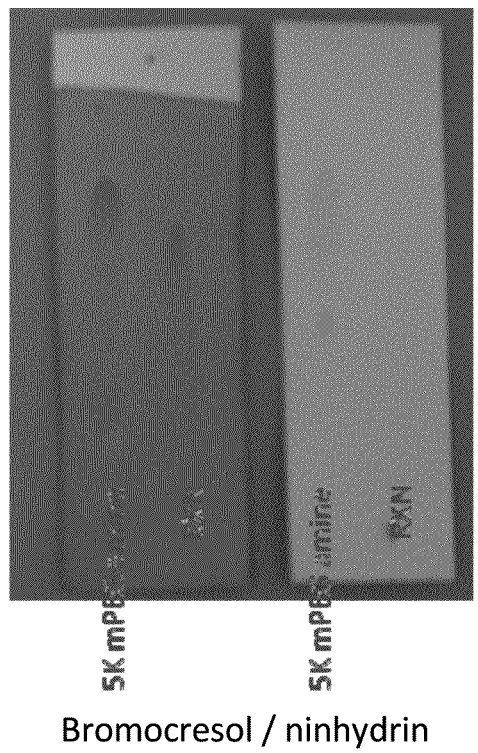
FIG. 18. Thin Layer chromatographic analysis of PEG-thapsic acid product and starting amino PEG. TLC mobile phase is 5:1 dichloromethane/methanol. Solid phase is Silica Gel 60 F254 on aluminum sheets. TLC was stained by Bromocresol Blue and Ninhydrin. Bromocresol blue stains blue for PEG bearing materials, Rf of 5K Amino PEG (s.m.)=0.76 and product thapsic acid-amino PEG conjugate (Fatty PEG, Product)=0.63. Starting material and product both stain bromocresol blue and 5K amino PEG stains positive for ninhydrin, the product does not.
Figure 19:
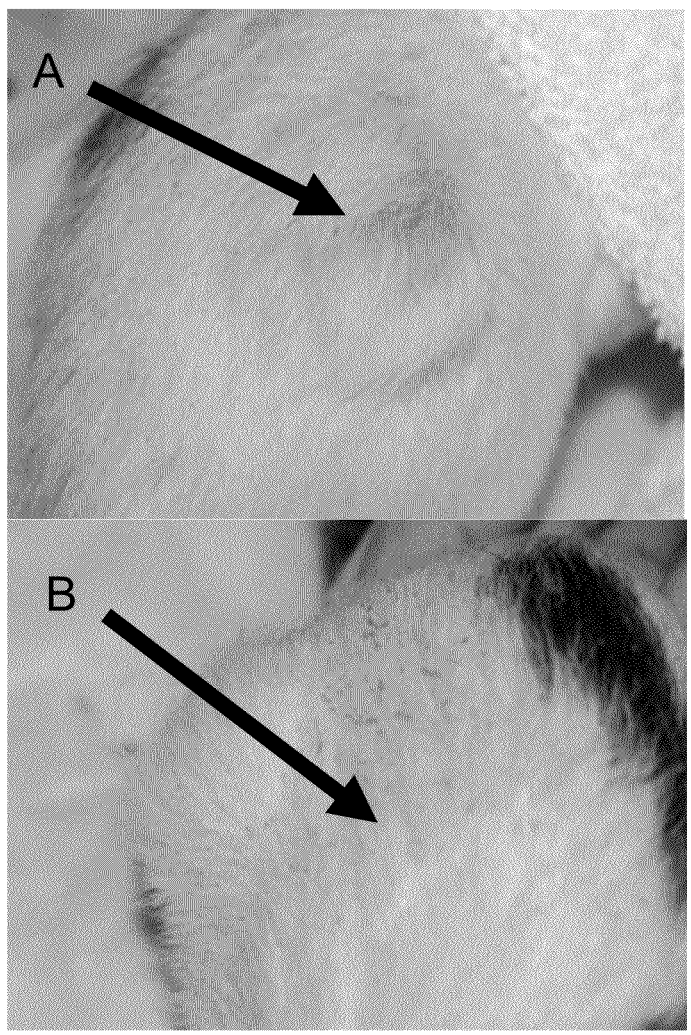
FIG. 19. Insoluble carrier causes skin necrosis whereas the soluble carrier does not. Shown are photographs of rat skins taken 3 weeks after subcutaneous injection of insoluble carrier (A) with PEG to fatty acid weight ratio of less than 10 and soluble carrier (B) with PEG to fatty acid weight ratio of greater than 10. The arrow in A shows that 15 mg of insoluble composition of U.S. Pat. No. 6,576,254 injected subcutaneously causes necrosis after 3 weeks (A, arrow) whereas no necrosis is observed in animals that received similar amount of soluble carrier of the present invention (B, arrow).
Figure 20:
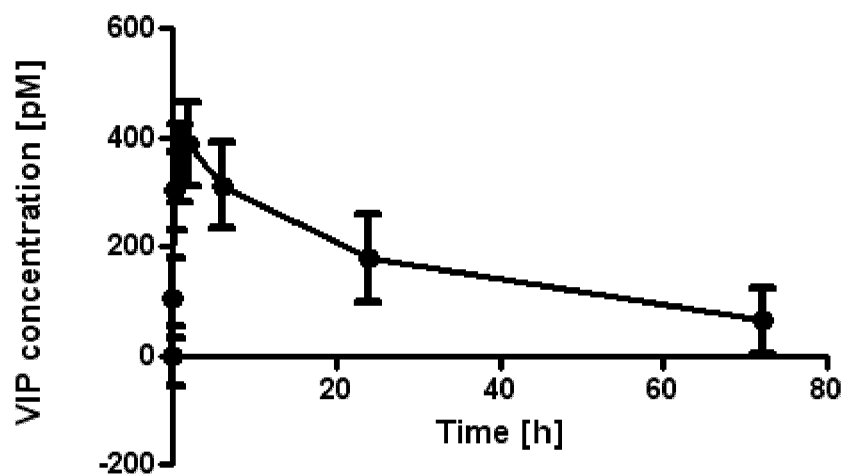
FIG. 20. Total VIP in the blood after subcutaneous administration of formulated VIP (20PLPEG555C18 containing 2% by weight of VIP). The 20PLPEG555C18 used in the formulation is a 20 kDa polylysine where 55% of the amino groups were reacted with PEG succinate of 5 kDa molecular weight and the remaining aminogroups were reacted with stearic acid or C18. The elimination half-life of VIP administered alone is just a few minutes (not visible in the graph) while the formulated VIP has half-life of more than 20 hours. Male Wistar rats were injected subcutaneous with 1 mg VIP alone or 1 mg VIP in 20PLPEG555C18 formulation (N=7) in phosphate buffered saline. Blood draws were done at given time points from the tail and protease inhibitor cocktail was added (Calbiochem, Cat#539131, La Jolla, Calif.). The total VIP (20PLPEG555C18 bound and unbound) are measured by Elisa kit from Peninsula (San Carlos, Calif.) and the background signal of rat serum were subtracted from all data points.

Synthesis of MPEG-thapsic acid: To make 5 kDa MPEG-thapsic acid, thapsic acid (1.15 g; 4 mmol, Sigma-Aldrich, St Louis, Mo.) was dissolved 50 mL of Dimethylformamide (DMF, Sigma-Aldrich) with 1.4 mL of triethylamine (TEA; 10 mmol, Fisher, Waltham, Mass.) and 1.65 g of N,N'-Dicyclohexylcarbodiimide (DCC, 8 mmol, Peirce, Rockford, Ill.). The solution was stirred for 15 min and N-hydroxysuccinimide (NHS; 920 mg; 8 mmol, Fisher) was added and stirred for another 15 min. MPEG amine (5 grams, 1 mmol of 5 kDa, Sunbio, South Korea) was dissolved in 45 mL of DMF by slight heating and added slowly into the activated thapsic acid solution over 15 minutes and stirred overnight. To determine if the reaction was complete, a 250 uL aliquot was removed, precipitated the MPEG with 5 mL of diethyl ether, dissolved in 1 mL of 1 N NaOH, acidified with HCL, extracted with dichloromethane (~2 mL), bottom layer collected, concentrated by a stream of air, added to diethyl ether (5 mL) to precipitate. The precipitate was collected, dissolved in 1 mL of dichloromethane, analyzed by thin layer chromatography (TLC). TLC mobile phase is 5:1 dichloromethane/methanol. Solid phase is Silica Gel 60 F254 on aluminum sheets. Visualized the following TLC stains by Bromocresol Blue and Ninhydrin. Bromocresol blue stains blue for PEG bearing materials, Rf of 5K Amino PEG (s.m.)=0.76 and product thapsic acid-amino PEG conjugate (Fatty PEG, Product) =0.63. Starting material and product both stain bromocresol blue and 5K amino PEG stains positive for ninhydrin, the product does not (see FIG. 18). Once reaction is complete, MPEG-thapsic was precipitated with ether (800 mL contained in a 1 L beaker, equipped with a stir bar), collected by vacuum filtration (Q8, filter paper, FisherBrand) and the precipitate in the filter was washed with additional diethyl ether (50 mL) The crude MPEG-thapsic acid was dissolved in 1N NaOH (20 mL) to remove excess activated carboxylic acid and the pH was restored back to acidic using HCl followed dilution with 50 ml water and extraction of MPEG-thapsic acid with Dichlomethane (100 mL) three times. The combined dichloromethane solution was dried with magnesium sulfate (50 g), filtered through a glass filter funnel (medium frit), and concentrated on a rotary evaporation under vacuum (bath temp ~50° C.). The residue was added to a stirring solution of diethyl ether (800 mL contained in a 1 L beaker, equipped with a stir bar) and the MPEG-thapsic acid solids were filtered through a Buchner funnel equipped with filter paper (Q8, qualitative, Fisher brand, pre-washed with ether) under house vacuum. The MPEG-thapsic acid product was dissolved in ethanol (50 ml) and washed with 10 volumes of 80% ethanol by ultra-filtration using 3K MWCU ultra-filtration cartridge (GE-Amersham, UFP-3-E-3MA, Batch #3-1067), followed with 10 volumes of water. The product was filter-sterilized using 0.2 um polysulfone filter (Nalgene, Rochester, N.Y.), and lyophilized giving 3.5 grams of materials.

Example 9

Synthesis of 20PLC16PEGF: This carrier is made up of 20 kDa polylysine (with degree of polydispersity of 1.2), wherein 90-99 percent of the TNBS reactive amino groups was reacted with 5 kDa MPEG-thapsic acid (see example 8). A warm stirring polylysine solution was prepared by dissolving 25 mg of Polylysine (Mw is 20 kDa with amine content=3.1 mmol/g as determined by TNBS assay, Cat #P7890, DPVIS=115, batch#017k5101, Sigma) in 50 ml of 200 mM HEPES and stirred in warmed oil bath at 40-50° C. Separately, MPEG-thapsic acid (320 mg, 0.060 mmol), N-hydroxysulfosuccinimide sodium salt (NHSS, 26.4 mg, 0.12 mmol, Fluka) and N-(3-Dimethylaminopropyl)-N'-ethylcarbodiimide (EDC, 23.2 mg, 0.12 mmol) were placed in 8 ml of 10 mM MES. The mixture was vortexed and incubated for 20 min. The activated MPEG-thapsic acid was added to the polylysine solution and stirred for 60 minutes. The activation of similar amount of MPEG-thapsic acid and addition to polylysine solution was repeated four more times at approximately 60 minutes apart and the mixture was stirred overnight. The reaction mixture concentrated to 50 ml and washed with 10 volumes of 80% ethanol followed by 10 volumes of water using ultra-filtration apparatus with 100 k MWCU ultra-filtration cartridge (GE-Amersham, UFP-100-E-3MA). The washes product was sterile filtered (0.2 micron, 115 mL, Nalgene) and lyophilized giving 400-500 mg of 20PLC16PEGF. TNBS assay of final material (1 mg/mL)

indicated an amine content of 7-10 nmol/mg (TNBS assay) indicating very little amino groups left in polylysine. GPC analysis using TosohG4000WXL eluted with PBS with 15% CAN at a flow rate of 0.6 mL/min indicated that the retention time is 11.9 min, indication a structure with diameter of 21 nm. This synthesis was repeated three times determine the reproducibility of the process. The following table shows the results of the triplicate synthesis of the carrier showing the reproducibility of the synthesis.

TABLE 3

|  | 20PLC16PEGF.; Lot # | | |
|---|---|---|---|
|  | A | B | C |
| Polylysine Degree of polymerization | 115 | 115 | 115 |
| Retention Time of finished Carrier (min) | 11.92 | 11.92 | 11.89 |
| Corresponding Carrier Diameter (nm) | 20.6 | 20.6 | 20.6 |
| Yield based on PL + PEG-Thapsic acid % (Amount) | 26% (430 mg) | 26% (420 mg) | 28%(450 mg) |
| NH2 left in Carrier (started at 3 umol/mg PL) | 7.1 nmol/mg | 10.3 nmol/mg | 10.5 nmol/mg |

Example 10

In order to fully characterized the type of load molecules that can be loaded into these carriers, a table showing the relative retention time of various molecules in reverse phase HPLC columns which reflects their relative hydrophobicity in acidic conditions (0.1% TFA). The results are a general guideline and should not be taken as absolute as can be seen with VIP. Most therapeutics has been run on reverse phase HPLC columns either during purifications after synthesis (or biosynthesis) or for analytical purpose. Therefore, this process of determining retention time on HPLC column does not constitute undue experimentation to enable the invention disclosed in the instant application. For the purpose of demonstration, candidate load molecules were eluted from reversed phase HPLC column (SynergiMaxRP 4×20 mm; Phenomenex, Torrance, Calif.) at a flow rate of 1.5 ml/min using a gradient of solvent A to B (25-50% B from 1-5 minutes) where A is water with 0.1% Trifluoroacetic acid (TFA)/5% Acetonitrile and solvent B is Acetonitrile with 0.1% TFA. Based on the binding studies in FIGS. 11-17, those with retention time of greater than 2.5 minutes under the above HPLC condition will likely demonstrate high affinity binding to the hydrophobic core carrier (Table 4) below

TABLE 4

List of retention times of various load molecules under the above chromatographic conditions and their corresponding Kd to the 20PLPRG555C18.

| Load molecules | Retention time (minutes) | Dissociation Constant (Kd) |
|---|---|---|
| Doxorubicin | 1.63 | >100 uM |
| Nociceptin | 1.42 | >100 uM |
| Terlipressin | 1.45 | >100 uM |
| Glucagon Like Peptide 1 (GLP-1; 3 kDa) | 3.2 | <500 nM* |
| Glucagon Like Peptide 2 (GLP-2; 3 kDa) | 2.46 | <500 nM* |
| Islet Amyloid Polypeptide (IAPP or Amylin; 3.6 kDa) | 2.36 | <900 uM* |
| Vasoactive Intestinal Peptide | 1.64 | <10 uM* |
| Human Growth Hormone (26 kDa) | 1.82 | >100 uM |
| Leptin (16 kDa) | 4.90 | <800 nM* |
| Insulin (5 kDa) | 1.79 | Not determined |

*Those with Kd in bold binds with high affinity or has Kd less than 100 uM.

To some extent, it is reasonable to extrapolate that it is almost always the case that load molecules eluting with retention time of greater than 2 minutes under this condition will have high affinity (Kd less than 100 uM) to the carrier, making the carrier sufficiently useful in prolonging the circulation half-lives of these molecules. One exception to the rule of using HPLC to predict affinity to the carrier is the vasoactive intestinal peptide. This peptide is quite hydrophilic in acidic condition (0.1% TFA) as can be seen from its retention time of 1.64 minutes. However in the presence of lipid at neutral pH it is known to assume an alpha helix conformation which is more compatible with hydrophobic lipid environment. Its high affinity to the carrier (20PLPEG555C18) in PBS may be due to the formation of more hydrophobic alpha helix. Although HPLC can be performed at neutral pH to be more predictive of the ability of the load molecule to bind to the hydrophobic core carrier of the present invention, it is a little challenging due to the broadening of the reverse phase HPLC peak under this condition. It is, however, quite proper and will still allow accurate prediction. This process is not an undue experimentation as the reverse phase HPLC is a standard and universal practice in the art. In addition to HPLC, assay for the binding of the carrier to the present composition can easily be performed by those with ordinary skill in the art as shown in example in FIGS. 11-17.

Example 11

Binding of load molecules to 20PLPEG555C18: Polypropylene micro-centrifuge tubes were prepared in triplicate. Aliquots (25 ul) of carrier stock (20PLPEG555C18; 100 mg/ml or 33 mg/ml) were placed in polypropylene micro-centrifuge tubes and 25 ul of water for the corresponding controls. Load molecules of various concentrations were added to the tubes so that the corresponding weight of load molecules will be between 2 to 30% of the weight of the carrier. To each tube, 25 ul of 10× Phosphate buffered saline was added and the total volume of the solution was made up to 250 ul. The solutions were incubated for 2 hours, followed by filtration through a 100 kDa molecular weight cut-off filter made up of regenerated cellulose (Microcon Ultracell YM-100; Millipore, Bedford, Mass.). The free unbound load molecules in the filtrate were analyzed by reverse phase HPLC using the conditions described above to generate Table 3. The total amount of load molecule loaded or the control is represented by the filtrate of the solution without the carrier. The amount of load molecules bound to the carrier is represented by the difference in the amount of load molecules between the filtrate without the carrier and the filtrate with the carrier. Prior to this analysis, the background filter binding was determined and accounted for whenever significant filter binding was found. FIGS. 11 to 17 were generated in this manner.

Although the foregoing invention has been described in some detail by way of illustration and example for the purposes of clarity of understanding, one skilled in the art will easily ascertain that certain changes and modifications may be practiced without departing from the spirit and scope of the appended claims.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:
1. A soluble hydrophobic-core carrier composition comprising:
    (i) a linear polymeric backbone;
    (ii) a plurality of hydrophilic polymeric protective side chains covalently linked and pendant to the linear polymeric backbone, wherein each hydrophilic polymeric protective side chain has a molecular weight between about 400 and about 20,000 Daltons; and
    (iii) at least one hydrophobic moiety covalently linked and pendant to the polymeric backbone;
    wherein the total weight ratio of the plurality of hydrophilic polymeric protective side chains and the hydrophobic moieties is in the range of 15:1 to 43:1 and wherein the composition is soluble in water.
2. The composition of claim 1, wherein the total weight ratio of the plurality of hydrophilic polymeric protective side chains and the hydrophobic moieties is in the range of 17:1 to 43:1 or in the range of 20:1 to 43:1.
3. The composition of claim 1, wherein at least 90% of the residues of the polymeric backbone are derivatized with either the plurality of hydrophilic polymeric protective side chains or the at least one hydrophobic moiety.
4. The composition of claim 1, wherein the hydrophilic polymeric protective side chains comprise polyethylene glycol, polypropylene glycol, a co-polymer of polyethylene glycol, a co-polymer of polypropylene glycol, polysaccharide, or alkoxy derivatives thereof.
5. The composition in claim 4, wherein the alkoxy derivative is methoxypolyethylene glycol, methoxypolypropylene glycol, a methoxylated co-polymer polyethylene glycol and polypropyleneglycol, or ethoxylated polysaccharide.
6. The composition of claim 1, wherein the linear polymeric backbone is selected from a group consisting of polylysine, polyaspartic acid, polyglutamic acid, polyserine, polythreonine, polycysteine, polyglycerol, natural saccharides, aminated polysaccharides, aminated oligosaccharides, polyamidoamine, polyacrylic acids, polyalcohols, sulfonated polysaccharides, sulfonated oligosaccharides, carboxylated polysaccharides, carboxylated oligosaccharides, aminocarboxylated polysaccharides, aminocarboxylated oligosaccharides, carboxymethylated polysaccharides, and carboxymethylated oligosaccharides.
7. The composition of claim 1, further comprising:
    (iv) a load molecule dissociably linked to the at least one hydrophobic moiety covalently linked and pendant to the linear polymeric backbone.
8. The composition of claim 7, wherein the hydrophilic polymeric protective side chains comprise methoxypolyethylene glycol.
9. The composition of claim 8, wherein the linear polymeric backbone comprises polylysine.
10. The composition of claim 9, wherein the at least one hydrophobic moiety comprises a fatty acid.
11. The composition of claim 10, wherein the load molecule is a therapeutic agent.
12. The composition of claim 11, wherein the therapeutic agent is a hydrophobic peptide, hydrophobic protein, or a hydrophobic drug.
13. The composition of claim 11, wherein the therapeutic agent is selected from GLP-1, GLP-2, leptin, islet amyloid polypeptide and vasoactive intestinal peptide.
14. The composition of claim 7, wherein the linear polymeric backbone is polylysine.
15. The composition of claim 7, wherein the at least one hydrophobic moiety comprises a fatty acid selected from the group of 6-carbon fatty acids to 36-carbon fatty acids, a fatty acid with at least one double bond, a multi-fatty acid-containing moiety, and an aromatic ring containing moiety.
16. The composition of claim 7, wherein the load molecule is hydrophobic peptide, hydrophobic protein, and hydrophobic drugs.
17. The composition of claim 7, wherein the load molecule is selected from GLP-1, GLP-2, leptin, islet amyloid polypeptide and vasoactive intestinal peptide.
18. The composition of claim 7, further comprising a targeting molecule covalently linked to the hydrophilic polymeric protective side chains.
19. The composition of claim 18, wherein the targeting molecule is selected from a group consisting of an antibody, fragment of an antibody, chimeric antibody, lectins, receptor ligands, proteins, enzymes, peptides, saccharides, quasi substrates of enzymes, cell-surface-binding compounds, and extracellular-matrix-binding compounds.
20. The composition of claim 7, further comprising a second plurality of protective chains covalently linked to the at least one hydrophobic moiety covalently linked and pendant to the linear polymer backbone.
21. A pharmaceutical composition, comprising:
    (i) a linear polymeric backbone;
    (ii) a plurality of hydrophilic polymeric protective side chains covalently linked and pendant to the linear polymeric backbone, wherein each hydrophilic polymeric protective side chain has a molecular weight between about 400 and about 20,000 Daltons;
    (iii) at least one hydrophobic moiety covalently linked and pendant to the linear polymeric backbone; and
    (iv) a load molecule dissociably linked to the at least one hydrophobic moiety covalently linked and pendant to the linear polymeric backbone,
    wherein the total weight ratio of the hydrophilic polymeric protective side chains and the hydrophobic moieties is in the range of 15:1 to 43:1 and wherein the composition is soluble in water and wherein the load molecule is a therapeutic agent.
22. A method of administering a therapeutic molecule to a subject comprising:
    administering to the subject a composition comprising:
    (i) a linear polymeric backbone;
    (ii) a plurality of hydrophilic polymeric protective side chains covalently linked and pendant to the linear polymeric backbone, wherein each hydrophilic polymeric protective side chain has a molecular weight between about 400 and about 20,000 Daltons;

(iii) at least one hydrophobic moiety covalently linked and pendant to the linear polymeric backbone;
(iv) a therapeutic molecule dissociably linked to the at least one hydrophobic moiety covalently linked and pendant to the linear polymeric backbone;
wherein the total weight ratio of the hydrophilic polymeric protective side chains and the hydrophobic moieties is in the range of 15:1 to 43:1 and wherein the composition is soluble in water.

23. A composition comprising a hydrophobic-core carrier wherein the hydrophobic-core carrier consists essentially of:
(i) a linear polymeric backbone;
(ii) a plurality of hydrophilic polymeric protective side chains covalently linked and pendant to the linear polymeric backbone, wherein each hydrophilic polymeric protective side chain has a molecular weight between about 400 and about 20,000 Daltons; and
(iii) at least one hydrophobic moiety covalently linked and pendant to the linear polymeric backbone; wherein the at least one hydrophobic moiety comprises an alkyl group of 6-36 carbons;
wherein the total weight ratio of the hydrophilic polymeric protective side chains and the hydrophobic moieties is in the range of 15:1 to 43:1 and wherein the hydrophobic-core carrier is soluble in an aqueous solution essentially free of organic solvents.

24. The composition of claim 23, wherein the hydrophobic-core carrier is a non-vesicle forming hydrophobic-core carrier.

25. The composition of claim 23, wherein the hydrophobic-core carrier does not form vesicles upon addition of cholesterol.

26. The composition of claim 23, wherein the at least one hydrophobic moiety is covalently linked to the linear polymeric backbone by a bond selected from a group consisting of an amide bond, an ester bond, a disulfide bond, and an ether bond.

27. The composition of claim 23, further comprising:
(iv) a load molecule dissociably linked to the at least one hydrophobic moiety covalently linked and pendant to the linear polymeric backbone.

* * * * *

UNITED STATES PATENT AND TRADEMARK OFFICE
CERTIFICATE OF CORRECTION

PATENT NO. : 8,999,930 B2  
APPLICATION NO. : 12/711564  
DATED : April 7, 2015  
INVENTOR(S) : G. M. Castillo et al.

Page 1 of 1

It is certified that error appears in the above-identified patent and that said Letters Patent is hereby corrected as shown below:

IN THE CLAIMS

| COLUMN | LINE | ERROR |
|---|---|---|
| 29 (Claim 1, line 10) | 31 | "the polymeric" should read --the linear polymeric-- |
| 29 (Claim 3, line 2) | 41 | "the polymeric" should read --the linear polymeric-- |

Signed and Sealed this  
First Day of March, 2016

Michelle K. Lee  
*Director of the United States Patent and Trademark Office*